(12) United States Patent
Giannotta et al.

(10) Patent No.: US 12,102,735 B2
(45) Date of Patent: Oct. 1, 2024

(54) BIOCOMPATIBLE HYDROGEL, PROCESS FOR PRODUCING SAME, AND USE THEREOF IN A MECHANICAL VISCOSUPPLEMENTATION SYSTEM

(71) Applicant: NVD, Biot (FR)

(72) Inventors: Jean-Claude Giannotta, Mougins (FR); Charles Calleja, Nantes (FR)

(73) Assignee: NVD, Biot (FR)

( * ) Notice: Subject to any disclaimer, the term of this patent is extended or adjusted under 35 U.S.C. 154(b) by 661 days.

(21) Appl. No.: 17/298,349

(22) PCT Filed: Dec. 2, 2019

(86) PCT No.: PCT/EP2019/083356
§ 371 (c)(1),
(2) Date: May 28, 2021

(87) PCT Pub. No.: WO2020/109628
PCT Pub. Date: Jun. 4, 2020

(65) Prior Publication Data
US 2022/0111124 A1    Apr. 14, 2022

(30) Foreign Application Priority Data

Nov. 30, 2018 (FR) ..................................... 1872196

(51) Int. Cl.
*A61L 27/16* (2006.01)
*A61L 27/18* (2006.01)
(Continued)

(52) U.S. Cl.
CPC .............. *A61L 27/52* (2013.01); *A61L 27/18* (2013.01); *A61L 27/20* (2013.01); *C08L 33/26* (2013.01); *A61L 2400/06* (2013.01)

(58) Field of Classification Search
None
See application file for complete search history.

(56) References Cited

U.S. PATENT DOCUMENTS

| | | |
|---|---|---|
| 5,798,096 A | 8/1998 | Pavlyk |
| 2002/0064512 A1 | 5/2002 | Petersen et al. |
| 2016/0319059 A1 | 11/2016 | Vlasov et al. |

FOREIGN PATENT DOCUMENTS

| | | | |
|---|---|---|---|
| EP | 0742022 A1 | 11/1996 | |
| EP | 3088011 A1 * | 11/2016 | ............. A61L 15/60 |

OTHER PUBLICATIONS

Chen Yu et al., "Biocpolymer Grafting: Synthesis and Properties," 2018, pp. 295-364. (Year: 2018).*

(Continued)

*Primary Examiner* — Brian Gulledge
(74) *Attorney, Agent, or Firm* — Seckel IP, PLLC

(57) ABSTRACT

A biocompatible hydrogel has between 0.3% and 30% by weight of dry matter of a copolymer formed at least from acrylamide, chitosan and N,N'-methylenebisacrylamide, as well as a diffusing agent. The diffusing agent is advantageously selected from the group consisting of inert ingredients which have biomechanical properties and active ingredients. A method of manufacturing the hydrogel by copolymerizing, washing, and adding the diffusing agent is provided, as well as a mechanical visco-supplementation system adapted for external or internal use that includes the hydrogel, and an external or internal mechanical visco-supplementation kit including an acrylamide and chitosan copolymer crosslinked with N,N'-methylenebisacrylamide, and a diffusing agent in solid phase or in suspension, the copolymer and the diffusing agent having been previously mixed in the form of a hydrogel during manufacture or being adapted to be mixed extemporaneously to form a hydrogel.

20 Claims, 13 Drawing Sheets chitosan-polyacrylamide chitosan-polyacrylamide-MBA

(51) Int. Cl.
    *A61L 27/20*     (2006.01)
    *A61L 27/52*     (2006.01)
    *A61L 27/54*     (2006.01)
    *A61L 27/58*     (2006.01)
    *C08L 33/26*     (2006.01)

(56) References Cited

OTHER PUBLICATIONS

Ghosh et al., Int. J. Pharm. Sci. Rev. Res., 2014, 25(1), pp. 219-223. (Year: 2014).*

International Search Report and Written Opinion dated Feb. 7, 2020 in counterpart application No. PCT/EP2019/083356; w/English partial translation and partial machine translation (total 19 pages).

Chen et al., "Grafting Modifications of Chitosan", in Biopolymer Grafting: Synthesis and Propoerties, Elsevier Inc, Amsterdam, The Netherlands, Jan. 1, 2018, pp. 295-364 (in English; D2 cited in the ISR).

Knapp et al., Clinical experiences with a new gel-like wound dressing after skin transplantation, Aktuelle Traumatologie, 1984, pp. 275-281 (English abstract; cited in the Specification).

Geliperm sheet, SMTL Dressings Datacard, revision date Dec. 16, 1997, last modified Mar. 28, 2002, www.dressings.org/Dressings/geliperm.html (in English; product mentioned in Knapp et al. 1984 abstract).

Ferreira et al., "Design of a Drug-Delivery System Based On Polyacrylamide Hydrogels, Evaluation of Structural Properties", Chem. Educator, 2001, No. 6, pp. 100-103 (in English; cited in the Specification).

Janssen et al., "Drugs and Polymers for Delivery Systems in OA Joints: Clinical Needs and Opportunities", Polymers, 2014, No. 6, pp. 799-819 (in English; cited in the Specification).

Croisier et al., "Chitosan-based biomaterials for tissue engineering", European Polymer Journal, vol. 49, No. 4, 2013, pp. 780-792 (in English; cited in the Specification).

* cited by examiner

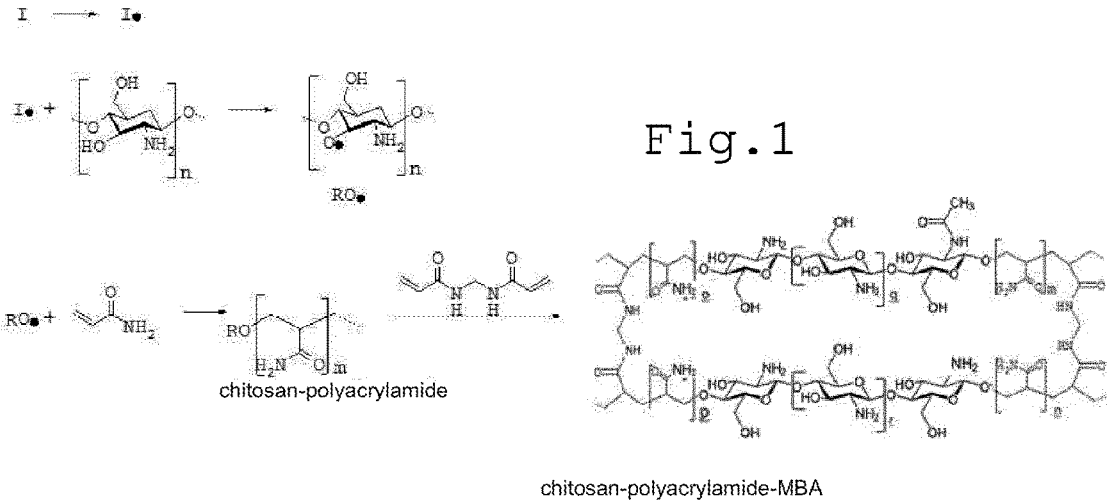
Fig.1
| Sample | Unit | Measured | theoretica |
|--------|------|----------|------------|
| V14 | % | 3.75 | 3.5 |
| V5 | % | 4.06* | 3.5 |
| V20 | % | 5.85 | 3.5 |
Fig.2A
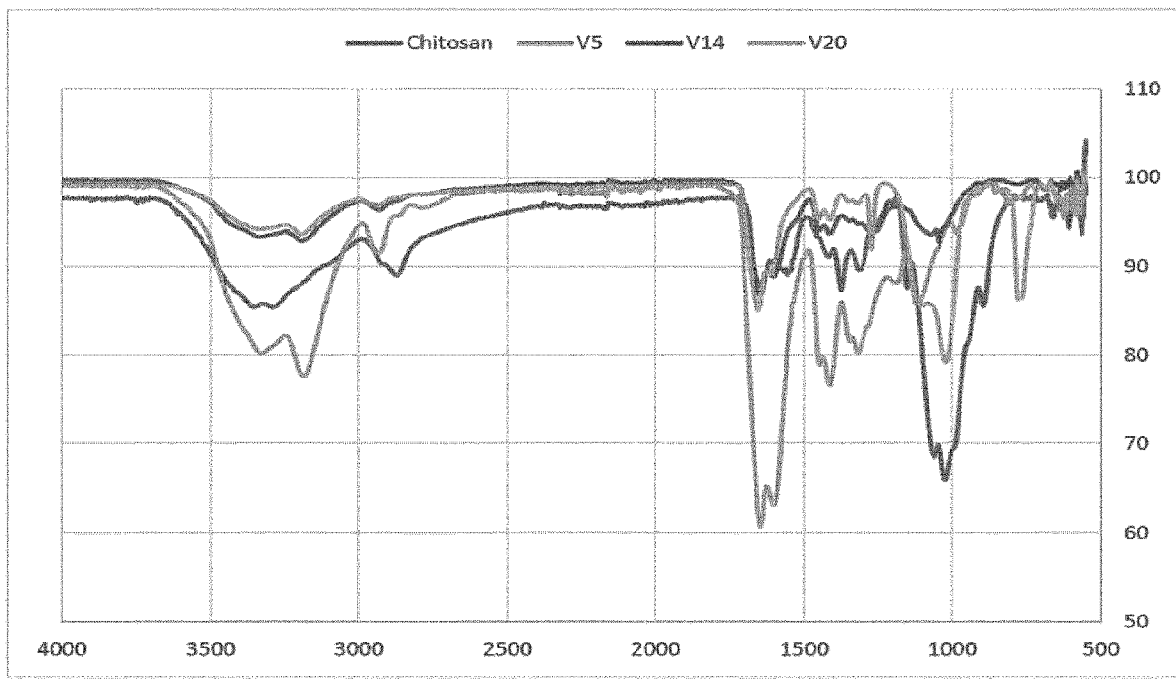
Fig.2B

| Wave number [cm$^{-1}$] | Attribution |
|---|---|
| 1316 | N-H stretching |
| 1413 | O-H stretching |
| 1450 | C-N stretching |
| 1602 | Amide (II) |
| 1648 | C-O stretching/ Amide (I) |
| 3182 | N-H extension |

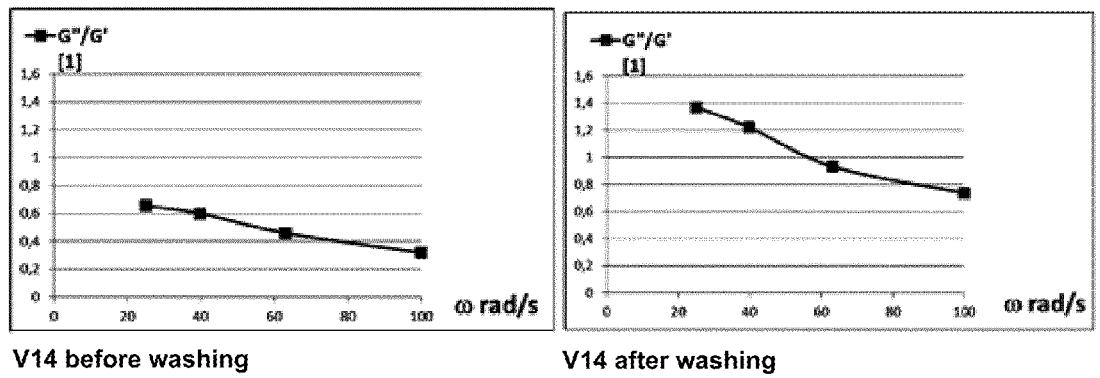
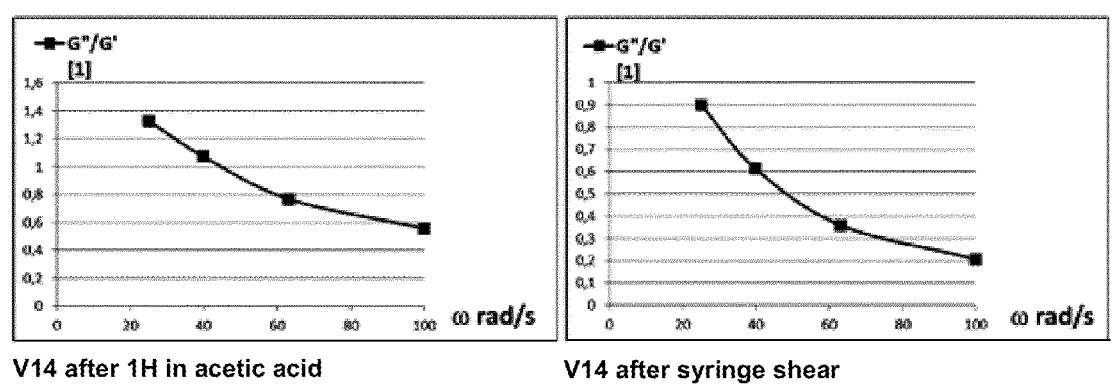
Fig.4
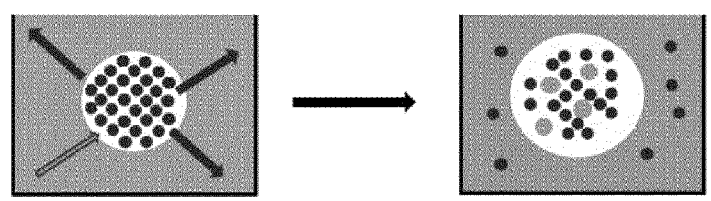
Fig.5

Biocompatibiliy XTT results of test item 5% copolymere Polyacrylamide-Chitosan (Ref: 190319 NVC-0)

| Hydrogel 5% Copolymere PAAG-CHITOSAN | | Replicates | Blank | Solvent control | Positive control (a) | Negative control (b) | Test extract (c) | | | |
|---|---|---|---|---|---|---|---|---|---|---|
| | | | | | | | 100% v/v | 66.7% v/v | 44.4% v/v | 29.6% v/v |
| Absortition (A450) | | 1 | 0.234 | 1.471 | 0.239 | 1.391 | 1.522 | 1.423 | 1.479 | 1.474 |
| | | 2 | 0.227 | 1.322 | 0.24 | 1.319 | 1.329 | 1.486 | 1.376 | 1.462 |
| | | 3 | 0.238 | 1.371 | 0.248 | 1.429 | 1.433 | 1.509 | 1.557 | 1.501 |
| | | 4 | 0.217 | 1.509 | 0.244 | 1.382 | 1.391 | 1.489 | 1.5 | 1.437 |
| | | 5 | 0.226 | 1.333 | | | | | | |
| | | 6 | 0.255 | 1.42 | | | | | | |
| Mean (A450) | | | 0.233 | 1.404 | 0.243 | 1.38 | 1.419 | 1.477 | 1.478 | 1.469 |
| SD | | | 0.012 | 0.069 | 0.003 | 0.039 | 0.07 | 0.032 | 0.065 | 0.023 |
| Mean (A450) blank corrected | | | | 1.171 | 0.01 | 1.147 | 1.186 | 1.244 | 1.245 | 1.236 |
| Mitochondrial dehydrogenase-activity (%) | | | | 100 | 1 | 98 | 101 | 102 | 102 | 102 |

SD   Standard Deviation
(a)   Latex extracted in DMEM 10% FBS
(b)   PP material extracted in DMEM 10% FBS
(c)   The test item was extracted under agitation in DMEM 10% FBS for 24 ± 2 h at 37 ± 1 °C and the test extract was cultured for 24 - 26 h with L929 cells at a final weight/volume ratio of 0.2 g test item / mL culture medium.

Fig.12A

Biocompatibiliy XTT results of test item 4% Polyacrylamide + silver ions (Ref: Noltrex Bioform)

| Hydrogel 4% PAAG with silver ions | | Replicates | Blank | Solvent control | Positive control (a) | Negative control (b) | Test extract (c) | | | |
|---|---|---|---|---|---|---|---|---|---|---|
| | | | | | | | 100% v/v | 66.7% v/v | 44.4% v/v | 29.6% v/v |
| Absortition (A450) | | 1 | 0.254 | 1.431 | 0.339 | 1.311 | 1.394 | 1.223 | 1.439 | 1.464 |
| | | 2 | 0.127 | 1.325 | 0.247 | 1.219 | 1.277 | 1.286 | 1.176 | 1.412 |
| | | 3 | 0.268 | 1.38 | 0.138 | 1.729 | 1.234 | 1.349 | 1.157 | 1.001 |
| | | 4 | 0.117 | 1.569 | 0.274 | 1.392 | 1.382 | 1.149 | 1.345 | 1.414 |
| | | 5 | 0.266 | 1.733 | | | | | | |
| | | 6 | 0.285 | 1.37 | | | | | | |
| Mean (A450) | | | 0.215 | 1.374 | 0.143 | 1.343 | 1.219 | 1.237 | 1.2878 | 1.479 |
| SD | | | 0.017 | 0.056 | 0.007 | 0.023 | 0.05 | 0.023 | 0.06 | 0.021 |
| Mean (A450) blank corrected | | | | 1.184 | 0.023 | 1.182 | 1.077 | 1.023 | 1.045 | 1.164 |
| Mitochondrial dehydrogenase-activity (%) | | | | 100 | 3 | 98 | 95 | 93 | 94 | 97 |

SD   Standard Deviation
(a)   Latex extracted in DMEM 10% FBS
(b)   PP material extracted in DMEM 10% FBS
(c)   The test item was extracted under agitation in DMEM 10% FBS for 24 ± 2 h at 37 ± 1 °C and the test extract was cultured for 24 - 26 h with L929 cells at a final weight/volume ratio of 0.2 g test item / mL culture medium.

Fig.12B

[poly(β-(1→4)-2-amino-2-deoxy-D-glucopyranose] chitosan molecule, according to Kurita (1998) obtained by deacetylation (DDA) of chitin

| Sample | acrylamide + bisacrylamide content (ppm) | acrylamide + bisacrylamide average content (ppm) |
|---|---|---|
| Ref 190319 NVC-0, batch V190322-A-3, T6 RT | < LQ | < LQ |
| | < LQ | |

Remark: LQ = 4ppm

BIOCOMPATIBLE HYDROGEL, PROCESS FOR PRODUCING SAME, AND USE THEREOF IN A MECHANICAL VISCOSUPPLEMENTATION SYSTEM

TECHNICAL FIELD OF THE INVENTION

The present invention relates to a biocompatible hydrogel. It further relates to a method for preparing such a hydrogel, a use of the hydrogel and a kit.

PRIOR ART

The medical use of hydrogels containing only polyacrylamide was first disclosed in the patent document published under the number EP0742022A, published on Nov. 13, 1996.

Other subsequently published patent documents have related to the use of biocompatible polyacrylamide hydrogels, in human health, as a filling agent, prostheses or visco-supplement (U.S. Pat. No. 7,678,146B, EP3088011A).

For some hydrogel formulations, clinical publications mention a sustainable biocompatibility of these hydrogels and the propensity thereof to form viscoelastic cross-linked structures of interest for the soft tissues in the case of external use, for example (wound care, Knapp et al, Clinical experiments with a new gel-like wound dressing after skin transplantation, Aktuelle Traumatology, December 1984, pp. 275-281) or articular use.

In vitro research has highlighted the possible ability of polyacrylamide-based crosslinked hydrogels to form reservoirs for controlled and delayed salting-out of biomolecules (Ferreira et al, Design of a Drug-Delivery System Based on Polyacrylamide Hydrogels, Evaluation of Structural Properties, Laboratories and Demonstrations, October 2000).

Numerous studies have shown the benefits of an in-situ supplementation of biomolecules conveyed in microcapsules, microspheres or vectors, contained in hydrogels and this is the case, within joints for example, with chitosan microspheres. Janssen el al, Drugs and Polymers for Delivery Systems in OA Joints: Clinical Needs and Opportunities, Polymers 2014, 6, pp. 799-819. One difficulty to be solved is to succeed in fastening, protecting and retaining biocompatible microcapsules in situ while avoiding the aggregates and thus initial excessive salting-out which can trigger possible inflammation.

Chitosan is a biocompatible and biodegradable biopolymer which has multiple biomedical uses, in particular in the three-dimensional crosslinked form as biomaterial (Croisier et al, Chitosan-based biomaterials for tissue engineering, European Polymer Journal, Volume 49, Issue 4, April 2013). The products of its degradation (glucosamine) are biocompatible, but the sustainability of the network is variable, in particular according to the applied mechanical and chemical constraints.

In this context, there is a growing need to design a mechanical support system for medical use which can meet the challenges of biocompatibility, biodegradability, visco-supplementation and in-situ carrying capacity.

SUMMARY OF THE INVENTION

Considering the foregoing, a technical problem, which the invention proposes to solve, is to produce for the health sector a new hydrogel which has improved properties relative to the chitosan or polyacrylamide hydrogels of the prior art, forming efficient support systems, having an in-situ carrying capacity, and likely to allow the release of a diffusing agent.

The first object of the solution of the invention to this problem is a hydrogel comprising, on the one hand, between 0.3% and 30% by weight of dry matter of a copolymer formed at least from acrylamide, chitosan and N,N'-methylenebisacrylamide and, on the other hand, a diffusing agent.

Thus, the hydrogel has a viscoelastic matrix structure which allows a prolonged mechanical hydration or visco-supplementation of the diffusing agent which is localized, fastened, protected and released by the hydrogel during the in situ degradation thereof. The hydrogel allows avoiding the aggregates of diffusing agents and, consequently, the initial excessive salting-out.

Advantageously, —the diffusing agent is selected from inert ingredients having interesting biomechanical properties or active ingredients, preferably substances of plant origin such as the genepi extracts, substances of marine origin such as the extracts of New Zealand green mussels (Perna canaliculus), orthosilicic acid, organic silicon, silanol, vitamins such as vitamins A, D3, E or C, metals such as gold or silver, analgesics such as lidocaine, xylazine, detomidine, non-steroidal anti-inflammatory drugs, such as flunixin, ketoprofen, aspirin, corticosteroids such as prednisolone, triamcinolone, hyaluronic acid, glycosaminoglycans, chondroitin sulphate, methylsulphonylmethane, bromelain, arnica, collagen, antioxidants, fatty acids —the diffusing agent is comprised in a cargo selected from microcapsules, microparticles and polymeric vehicles, preferably biodegradable microcapsules; —the hydrogel is substantially free of pyrogenic agents; —the mass ratio of acrylamide to chitosan is comprised between 1/1 and 1/8; —the mass ratio of N,N'-methylenebisacrylamide to acrylamide is comprised between 1/50 and 1/1000, preferably comprised between 1/100 and 1/500; and —the following ratio of the constituents in % by weight of the total weight of the hydrogel: acrylamide comprised between 0.3% and 20%; chitosan comprised between 0.0375% and 10%, N,N'-methylenebisacrylamide comprised between 0.004% and 0.4%; diffusing agent comprised between 0.001% and 30%; and $H_2O$ up to 100%.

The second object of the invention is a method for manufacturing a hydrogel as defined above, comprising the following steps of: copolymerizing acrylamide and chitosan, in the presence of N,N'-methylenebisacrylamide and a radical initiator, in an aqueous medium, to obtain a copolymer; washing the copolymer with water to obtain a washed copolymer; and adding a diffusing agent to obtain the hydrogel.

In a preferred embodiment, the method comprises the following steps: copolymerization of acrylamide and chitosan, in the presence of N,N'-methylenebisacrylamide, a diffusing agent, and a radical initiator, in an aqueous medium, to obtain a copolymer incorporating the diffusing agent then washing the copolymer incorporating the diffusing agent with water to obtain the hydrogel.

Advantageously, the method comprises the following steps: copolymerization of acrylamide and chitosan introduced with a mass ratio comprised between 1/1 and 1/8, at a temperature comprised between 20 and 60° C., preferably between 40 and 60° C., in the presence of N,N'-methylenebisacrylamide which is introduced with a mass ratio relative to the acrylamide comprised between 1/50 and 1/1000, preferably comprised between 1/100 and 1/500, and of a radical initiator with a mass ratio relative to the acrylamide between 1/100 and 1/10 selected from potassium persulphate or ammonium persulphate, possibly in association with tetramethylethylenediamine with a mass ratio relative to acrylamide between 1/2000 and 1/20, in an aqueous medium to obtain a copolymer; washing the copolymer with water to obtain a washed copolymer; and adding the diffusing agent between 0.001% and 30% by weight of the total weight of the hydrogel, the diffusing agent being selected from inert ingredients having interesting biomechanical properties or active ingredients, these agents preferably being substances of plant origin such as the genepi extracts, substances of marine origin such as the extracts of New Zealand green mussels (Perna canaliculus), orthosilicic acid, organic silicon, silanol, vitamins such as vitamins A, D3, E or C, metals such as gold or silver, analgesics such as lidocaine, xylazine, detomidine, non-steroidal anti-inflammatory drugs, such as flunixin, ketoprofen, aspirin, corticosteroids such as prednisolone, triamcinolone, hyaluronic acid, glycosaminoglycans, chondroitin sulphate, methylsulphonylmethane, bromelain, arnica, collagen, antioxidants, fatty acids, possibly comprised in a cargo selected from microcapsules, microparticles or polymeric vehicles, preferably biodegradable microcapsules, to obtain the hydrogel.

The third object of the invention is the use of a hydrogel as defined above, in a mechanical visco-supplementation system, for external or internal use.

Advantageously, —the visco-supplementation system is a lubricant; —the visco-supplementation system is a cross-linked matrix with a carrying or storage capacity; —the visco-supplementation system is a moisturizer; —the diffusing agent begins to diffuse between the 2nd and the 30th day after administration, preferably between the 10th and the 20th day, in particular from the 15th day; and —the diffusing agent is released over a period comprised between 2 weeks and 12 months, preferably between 1 month and 6 months.

The fourth object of the invention is an external or internal mechanical visco-supplementation kit comprising an acrylamide and chitosan copolymer crosslinked with N,N'-methylenebisacrylamide, and a diffusing agent in solid phase or in suspension, said copolymer and said diffusing agent being previously mixed, during the manufacture, in the form of a hydrogel or mixed extemporaneously to form a hydrogel.

BRIEF DESCRIPTION OF THE FIGURES

The invention will be better understood on reading the following non-limiting description, written with reference to the appended drawings, in which:

FIG. 1 schematizes the grafting reaction of chitosan onto polyacrylamide by the intervention of a radical reaction (creation of free radicals using a radical initiator, denoted I), and the crosslinking of the copolymer under the action of N,N'-methylenebisacrylamide, according to the invention, o, p, q, r, n and m are the numbers of monomer units;

FIG. 2A is a table which shows, after drying the hydrogels (50° C. for more than 12 hours, and weighing the dry matter, the weight percentage of dry matter. The hydrogel V14 is the copolymer of the invention (3.75% dry matter), the hydrogel V5 is pure polyacrylamide and V20 is the copolymer with the diffusing agent.

FIG. 2B represents a comparison of the Fourier transform infrared spectra (FT-IR), detailed in Example 2, of the chitosan-polyacrylamide-MBA copolymer (V14) (MBA for N,N'-methylenebisacrylamide) present in the hydrogel of the invention without diffusing agent, then the V20 with diffusing agent, of a "pure" polyacrylamide gel (V5) and "pure" chitosan (Chitosan);

Figures 2C, 2D:
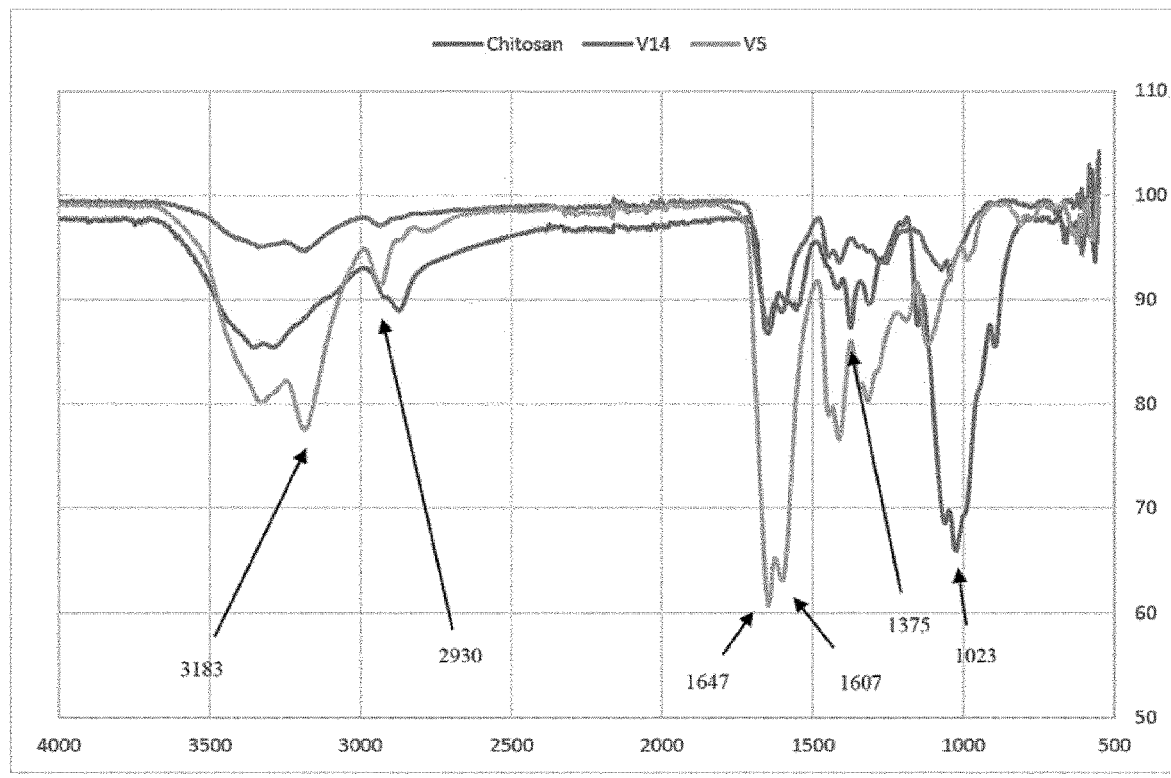
FIG. 2C represents a comparison of the Fourier transform infrared spectra (FT-IR), detailed in Example 2, of the chitosan-polyacrylamide-MBA copolymer (V14) (MBA for N,N'-methylenebisacrylamide) present in the hydrogel of the invention, of a "pure" polyacrylamide gel (V5) and "pure" chitosan (Chitosan)
Figure 3A:
Figure 3B:
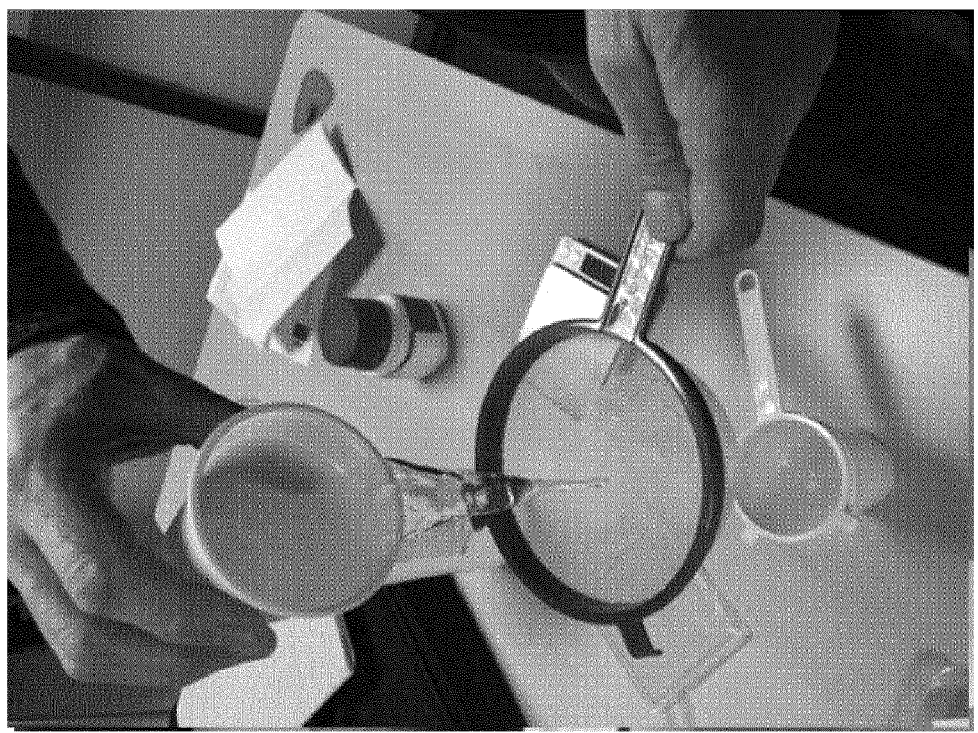
Figure 6:
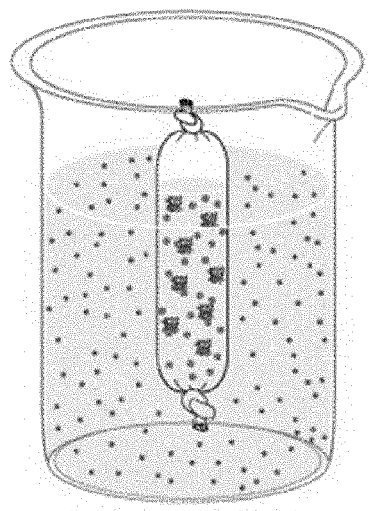
Figure 7A:
Figure 7B:
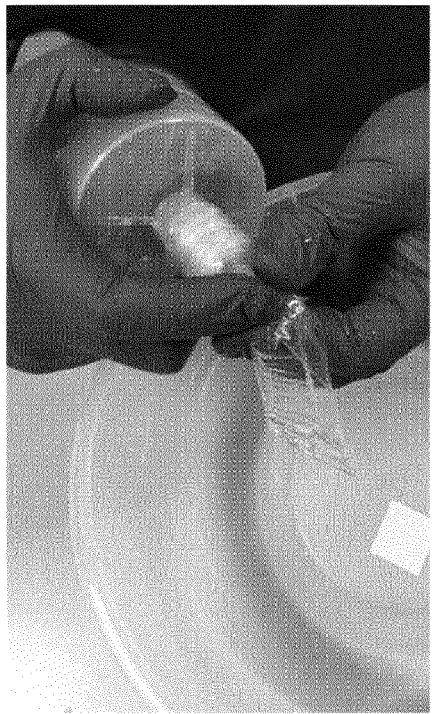
Figure 7C:
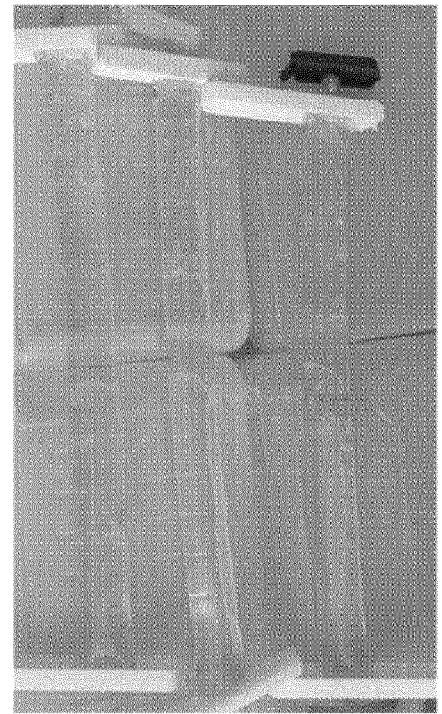
Figure 8:
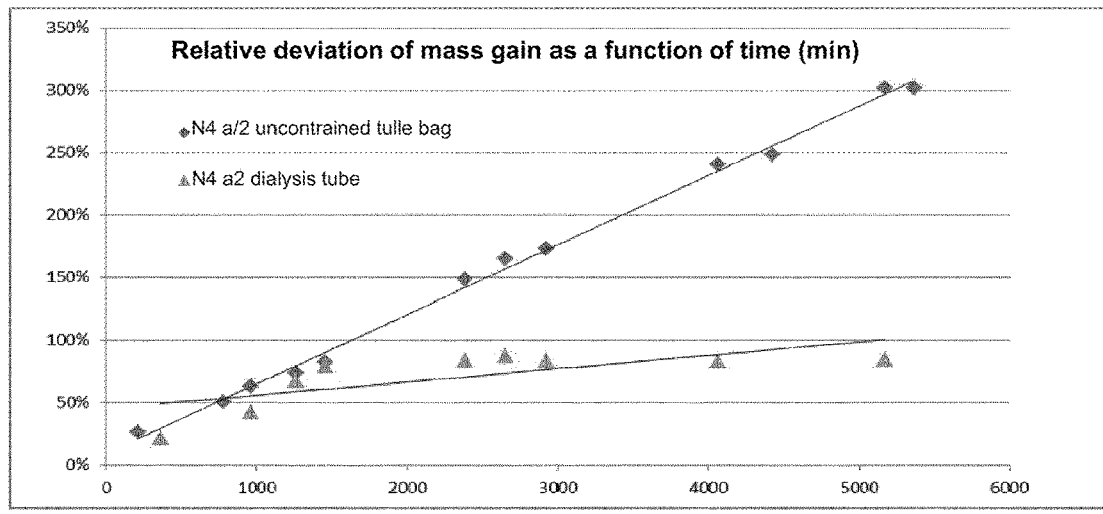
Figure 9:
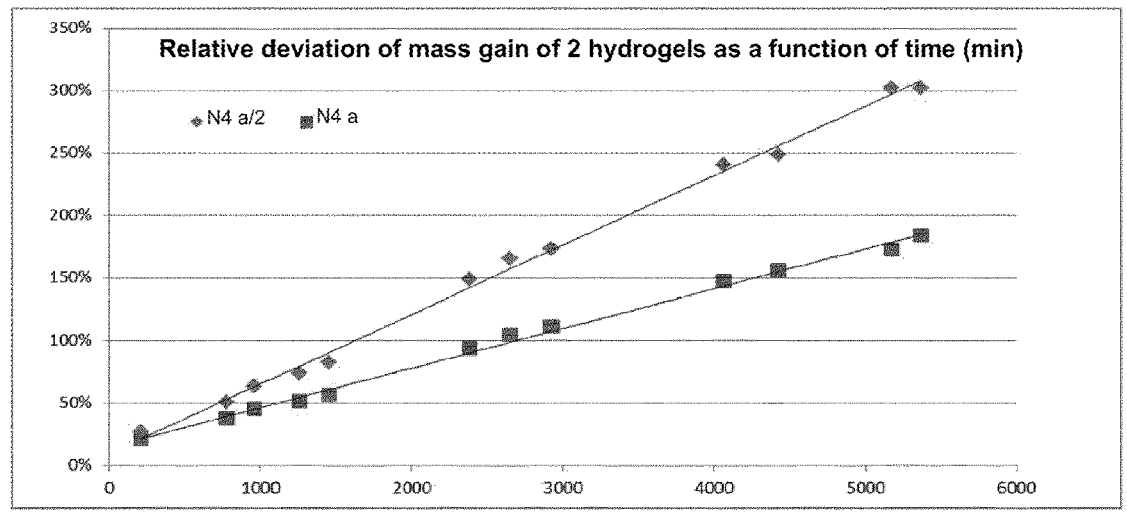
Figure 10:
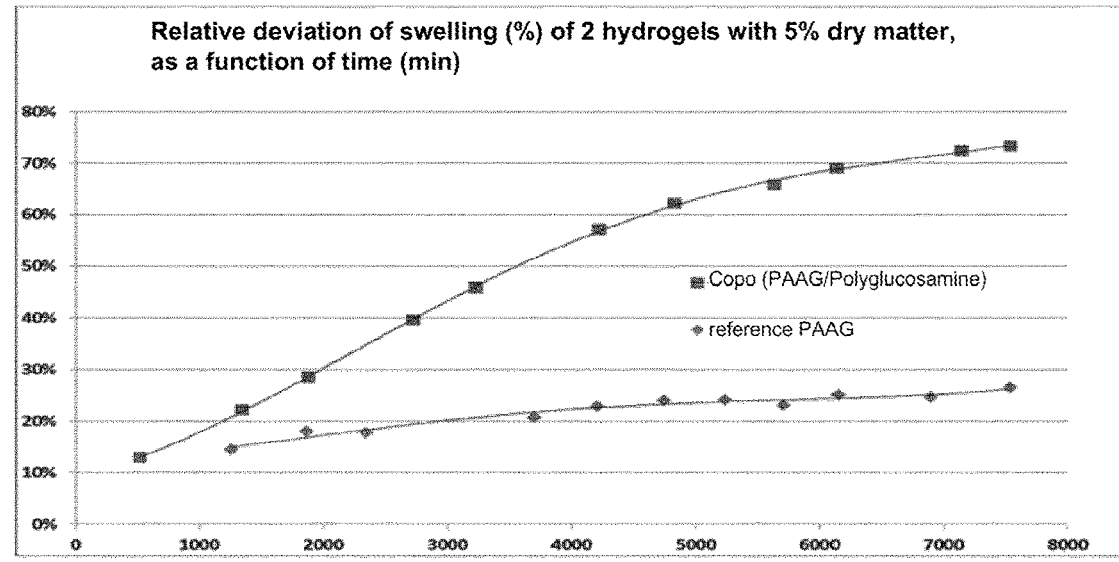
Figure 11A:
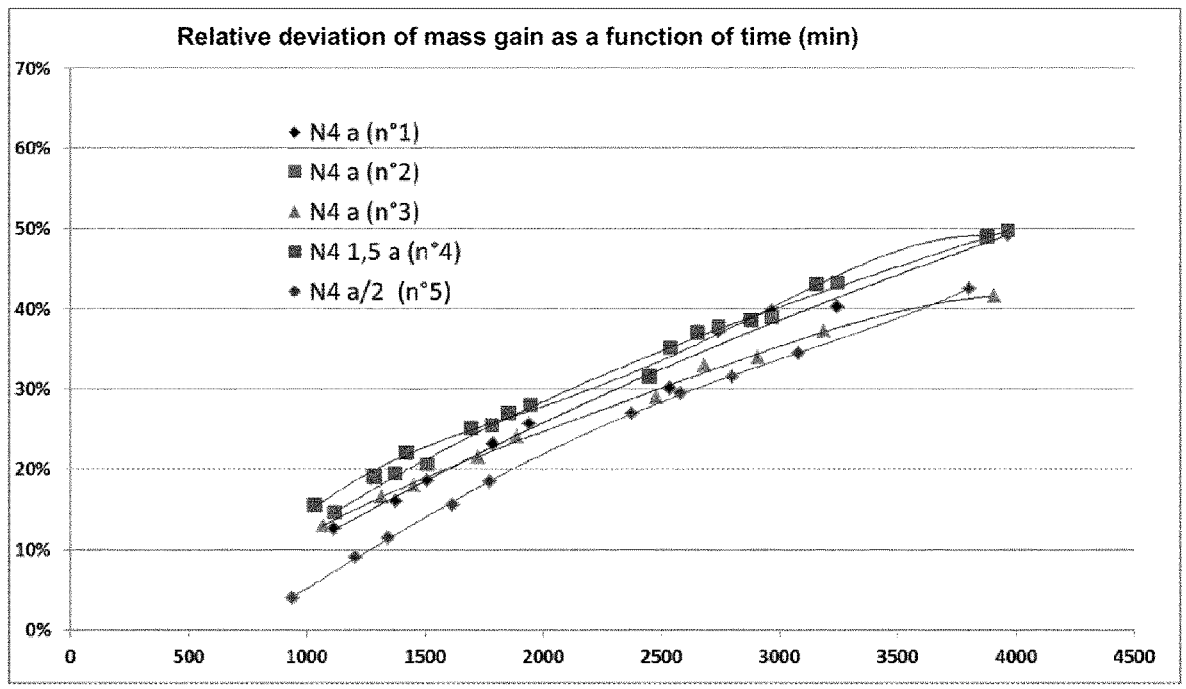
Figure 11B:
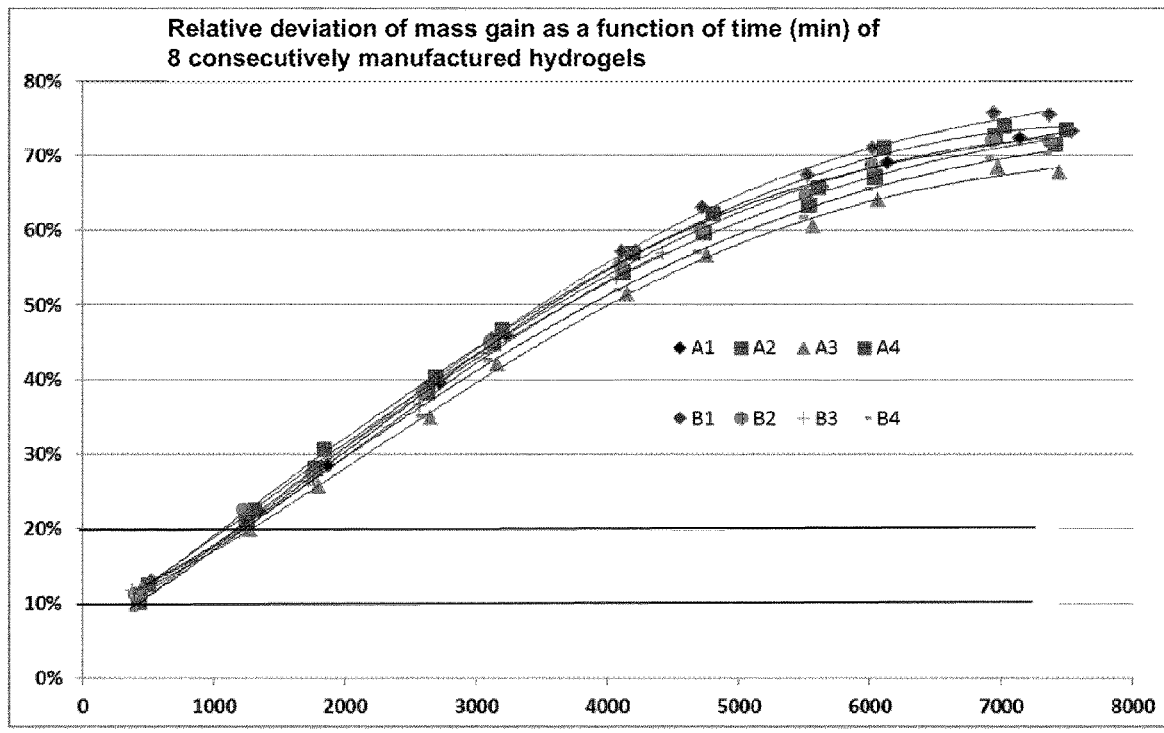
Figure 13:
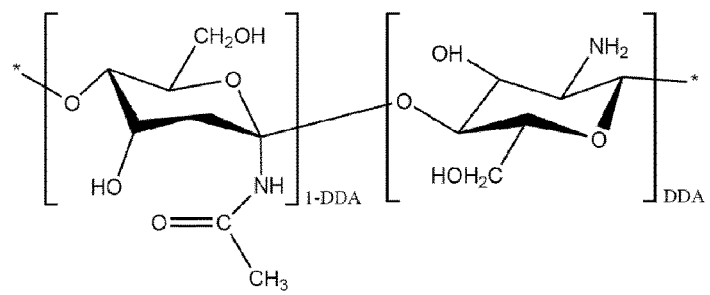
Figure 14:
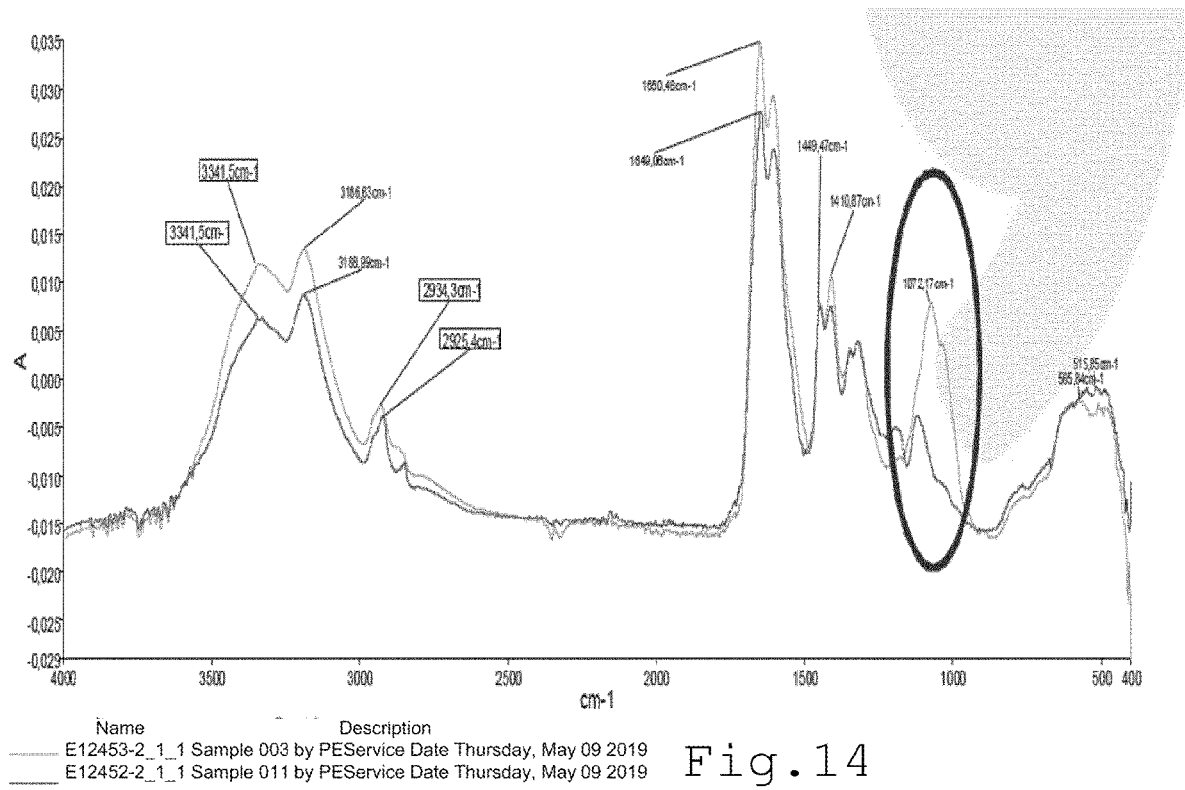
Figure 15A:
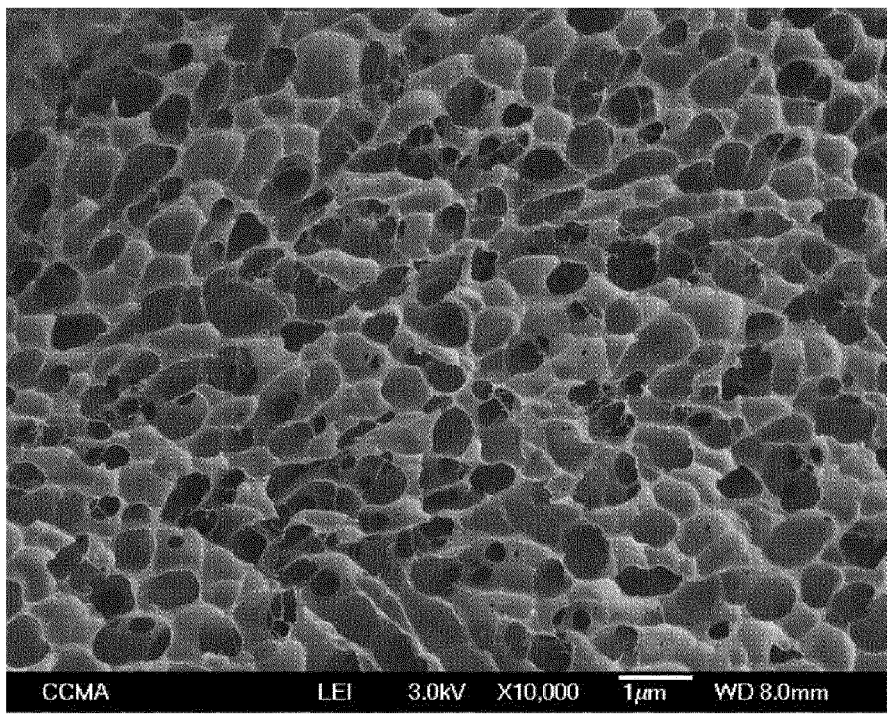
Figure 15B:
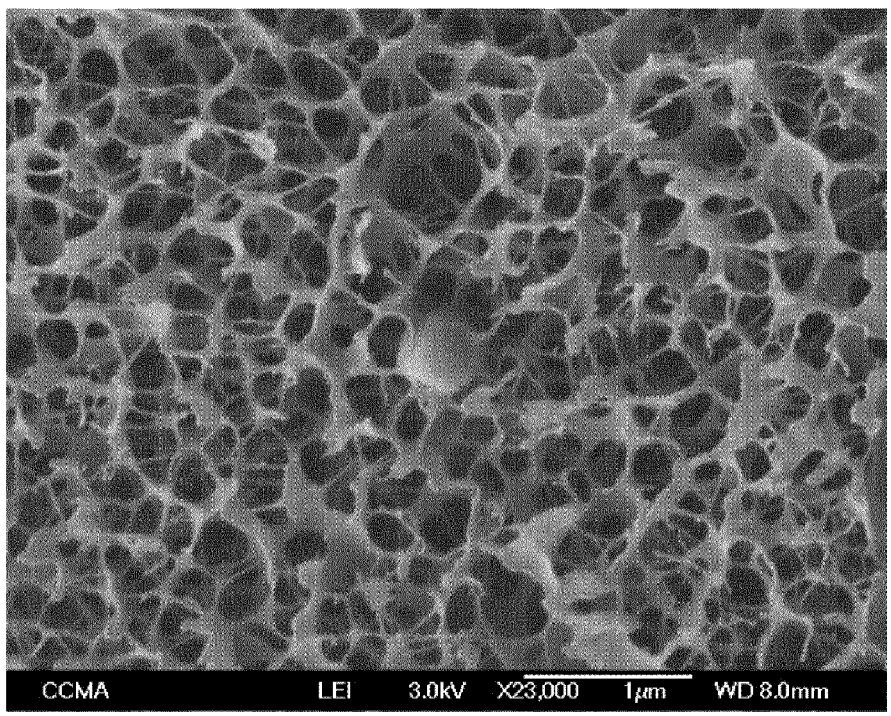
Figures 16, 17:
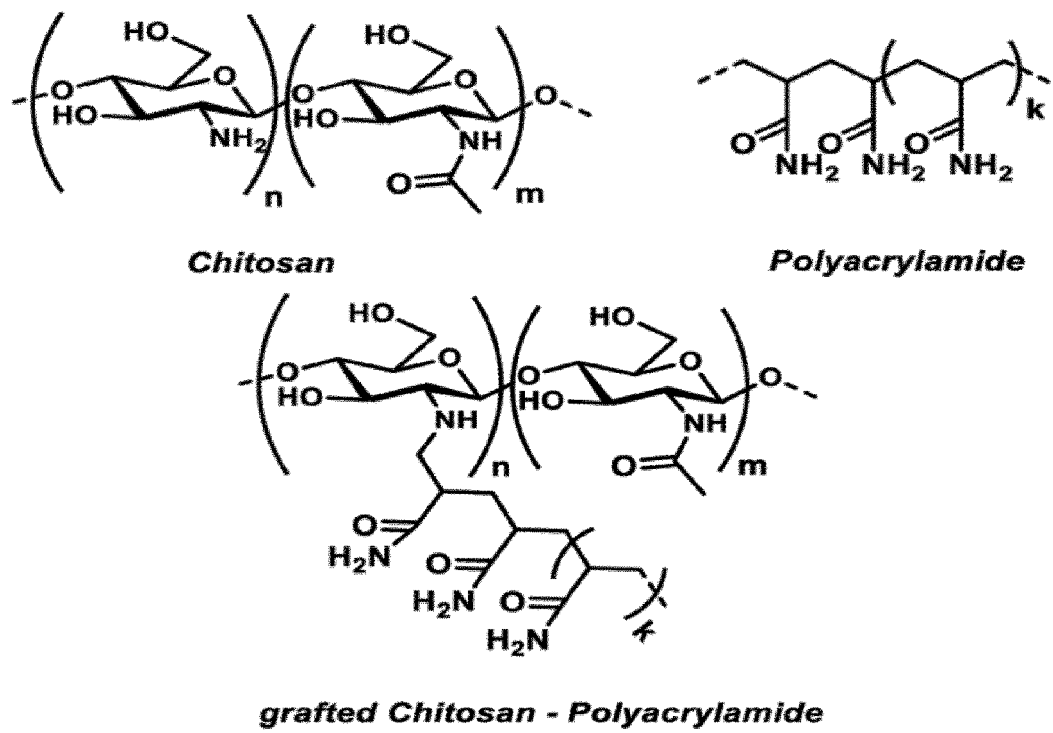
Figure 18A:
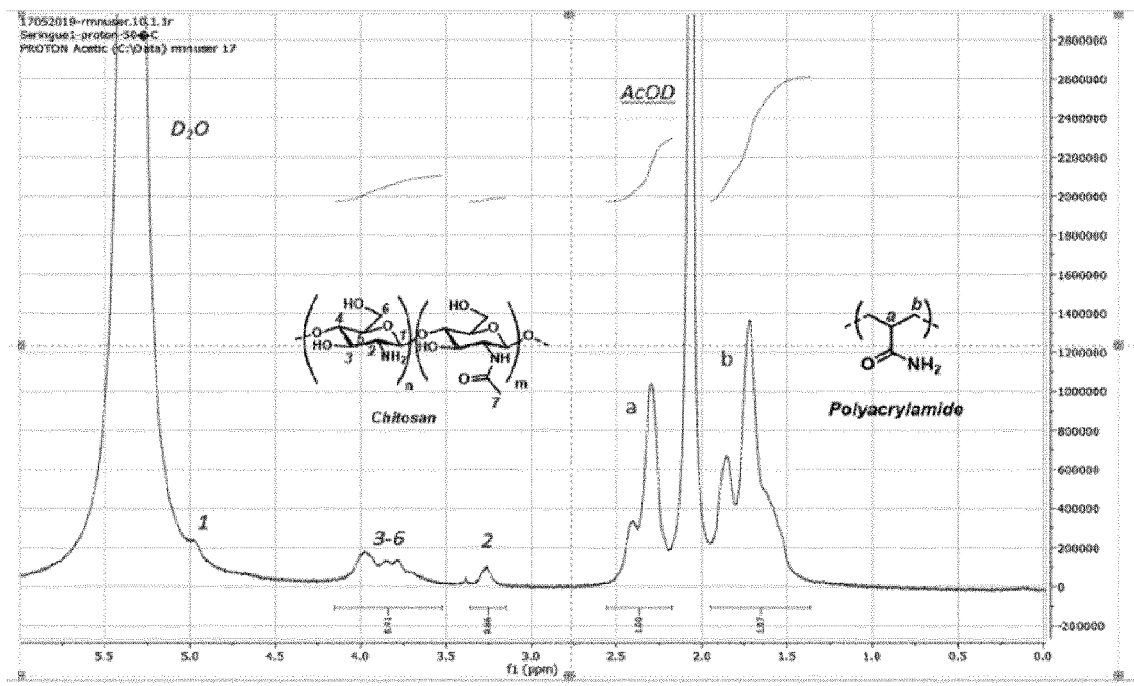
Figure 18B:
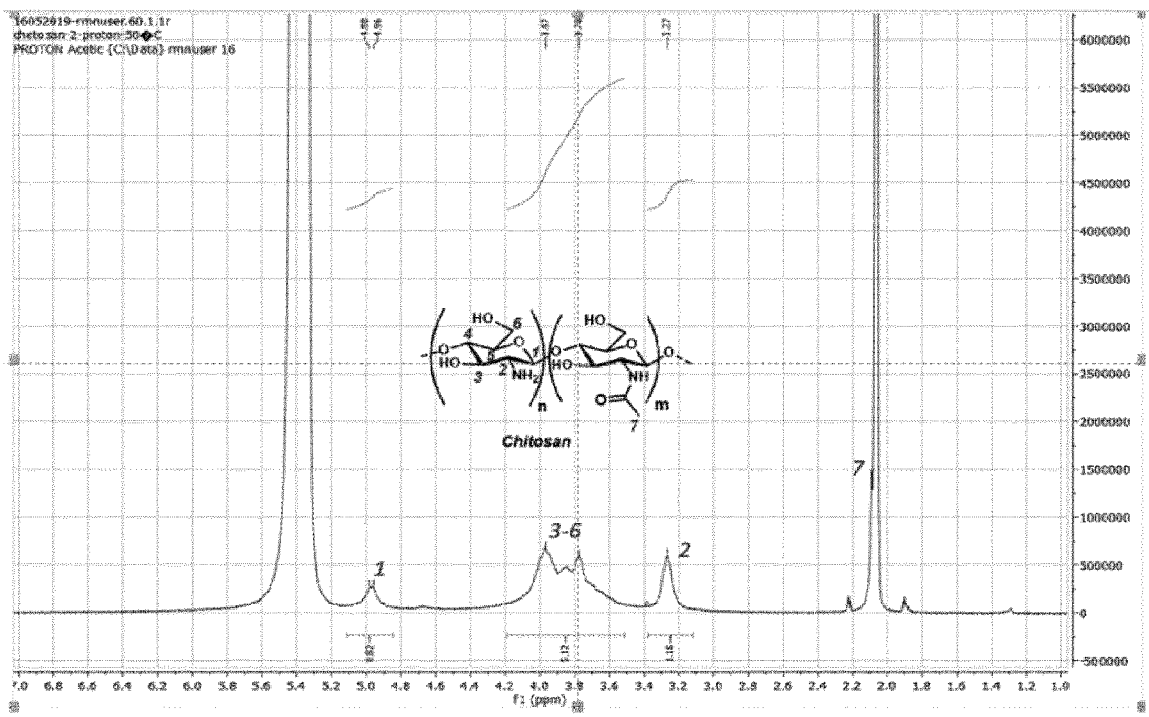
Figure 18C:
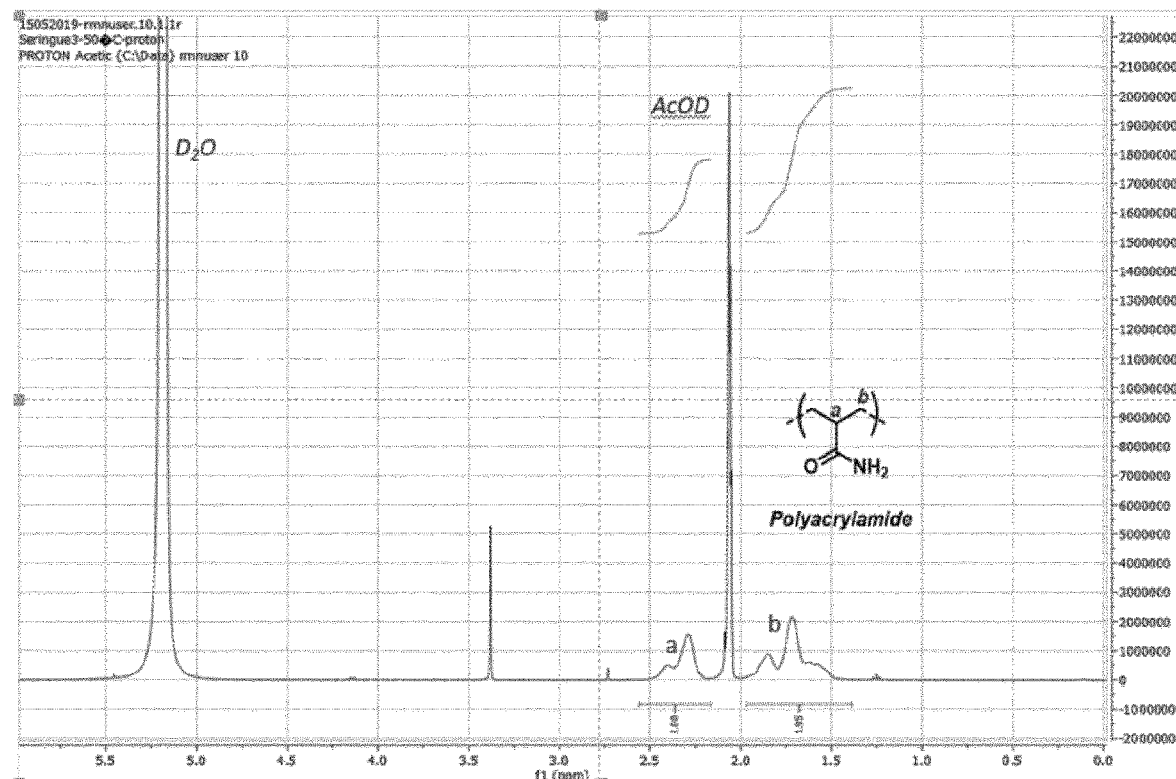

The table of FIG. 2D lists the majority peaks of FT-IR of the chitosan-polyacrylamide-MBA copolymer;

FIG. 3A shows a dissolution test of the copolymer present in the hydrogel of the invention, in acetic acid, as described in Example 2 and FIG. 3B illustrates the absence of dissolution of the copolymer in the acetic acid by filtration of the hydrogel after the dissolution test of described in Example 2;

FIG. 4 shows the loss tangents following the viscoelasticity measurements, in the different cases studied for the copolymer of the invention;

FIG. 5 is a diagram which illustrates the step of washing the copolymer during which the residual monomers, represented by black circles, leave the three-dimensional network formed by the copolymer and represented in white, and are replaced by water molecules (gray circles) by an osmotic phenomenon;

FIG. 6 is a diagram which illustrates the washing of the copolymer in a dialysis membrane;

FIG. 7A is a photograph which shows the placement of the dialysis membrane on the neck of an injection gun;

FIG. 7B is a photograph which shows the filling of the dialysis membrane using the injection gun;

FIG. 7C is a photograph which shows the closure of the dialysis membranes by clips and knots;

FIG. 8 compares the relative deviation of mass gain, in percentage, of an unconstrained hydrogel in a tulle bag (black diamonds) and a hydrogel constrained in a dialysis membrane (gray triangles);

FIG. 9 represents the relative deviation of the mass gain of two hydrogels, in percentage, as a function of time, in minutes, when washing the copolymer in a dialysis membrane;

FIG. 10 represents the relative deviation of the mass gain, in percentage, as a function of time in minutes, of two hydrogels of 5% dry matter, of a copolymer as defined in the invention (squares), and of a polymer of the prior art, a reference polyacrylamide-MBA (diamonds), in the presence of water;

FIG. 11A represents the relative deviation of the mass gain, in percentage, as a function of time in minutes, of different copolymers as defined in the invention and N4 a (N*1): Hydrogel 4.8% PAAG-Chitosan copolymer,
N4 a (N*2): Hydrogel 4.8% PAAG-Chitosan copolymer,
N4 a (N*3): Hydrogel 4.8% PAAG-Chitosan copolymer,
N4 3a/2 (N*4): Hydrogel 4.8% PAAG-Chitosan copolymer, with +50% of MethylBisAcrylamide cross-linking agent,
N4 a/2 (N*5): Hydrogel 4.8% PAAG-Chitosan copolymer, with 50% of MethylBisAcrylamide cross-linking agent;

FIG. 11B represents the relative deviation of the mass gain, in percentage, as a function of time in minutes, of 8 copolymer hydrogels which are consecutively manufactured as defined in the invention;

FIGS. 12A and 12B show tables from XTT assays "In Vitro Cytotoxicity Assay, Cell Growth Analysis via XTT-Staining and Grading Score Analysis";

FIG. 13 illustrates the formula of chitosan, obtained by deacetylation of chitin. Chitosan contains glucosamine (right group in the Figure);

FIG. 14 is a graph which corresponds to the FTIR spectrum of a sample referenced 1904-E0012452 of a 2.5% polyacrylamide hydrogel (in dark gray) and of a sample according to the invention referenced 1904-E0012453 of a 5% polyacrylamide-chitosan copolymer hydrogel (in light gray);

FIG. 15A is a scanning electron microscopy (SEM) image illustrating the crosslinked structure of the copolymer of the invention, after cryogenics and FIG. 15B is a SEM image illustrating the crosslinked structure of the hydrogel of the invention, after cryogenics, in which a particle of the diffusing agent appears in an alveolus of the three-dimensional network;

FIG. 16 is a table which indicates the contents of residual monomers of acrylamide and methyl-bis-acrylamide, after dialysis. These values are below the measurement limits of 4 ppm;

FIG. 17 illustrates the fact that the copolymer of the hydrogel according to the invention is formed by creating a macromolecular chain which is then organized in the form of a three-dimensional network thanks to the crosslinking agent (methyl-bis-acrylamide);

FIGS. 18A, 18B and 18C are NMR curves of the 5% polyacrylamide-chitosan copolymer (FIG. 18A) which show several distinctive points, in particular specific to chitosan in 1% solution at 3.2, 3.6 and 4.9 ppm (FIG. 18B) and in a significant proportion relative to the NMR of the 2.5% polyacrylamide hydrogel alone (FIG. 18C).

DETAILED DESCRIPTION OF THE INVENTION

According to the present invention, the terms "comprised between . . . and . . . " used to define intervals of values should be understood as integrating the lower and upper limits of these intervals. The terms "% by weight" should be understood as "% by weight relative to the total weight of the hydrogel".

According to a first object, the invention relates to, on the one hand, a hydrogel for the health sector comprising between 0.3% and 30% by weight of dry matter of a copolymer formed at least from acrylamide, chitosan and N,N'-methylenebisacrylamide and, on the other hand, a diffusing agent.

A "hydrogel" is a gel, that is to say, a three-dimensional network of solids diluted in a fluid, whose fluid is water (generally 80% or more by weight of the total weight of the hydrogel). The three-dimensional network of solids is generally a network of polymers. The latter are insoluble in water, but are capable of swell substantially in the presence of a large amount of water.

With reference to FIG. 1, the hydrogel of the invention comprises or consists of a three-dimensional molecular network trapping water molecules and onboarding a diffusing agent. The three-dimensional molecular network is formed by a chitosan-polyacrylamide-MBA copolymer. Water is present in the hydrogel in an amount of 70 to 99.7% by weight, preferably in an amount of 90 to 96% by weight of water, excluding the diffusing agent. The copolymer hydrogel according to the invention has a carrying capacity of diffusing agents, in particular of submicron capsules. The microstructure of the three-dimensional network of this hydrogel has alveoli whose size is compatible with the carried particles, which polyacrylamide gels made according to the prior art do not propose. Furthermore, and as shown in the examples of the present description, the hydrogel according to the invention has a capacity 3 times greater in carrying water (hydrophilic swelling) relative to a hydrogel of the same concentration of polyacrylamide only. So, less substance is needed with a copolymer hydrogel to offer as much hydration as with a polyacrylamide gel with equal initial dry matter concentrations.

The hydrogel of the invention is "biocompatible", that is to say, it does not degrade the biological medium in which it is used. This biocompatibility comes from the large amount of water which is absorbed by the hydrogel and the non-toxic three-dimensional structure formed by a chitosan and polyacrylamide copolymer crosslinked with N,N'-methylenebisacrylamide.

The hydrogel of the invention is "biodegradable" in the sense that it is degraded forming entities which are not harmful to the environment in which it is located. In particular, one of the degradation products of the hydrogel of the invention, for example containing chitosan, is glucosamine, which is also naturally produced by the body from glucose and glutamine. Glucosamine plays a leading role in maintaining the integrity of the cartilage in all joints. It supports the lubricating action of the synovial fluid, a natural lubricant for the joints.

The hydrogel of the invention is a chitosan-polyacrylamide-MBA hydrogel comprising a diffusing agent. This hydrogel therefore comprises a chitosan-polyacrylamide-MBA copolymer formed at least from acrylamide, chitosan and N,N'-methylenebisacrylamide.

Acrylamide is a monomer of synthetic origin. During polymerization, the monomers come together in a macromolecule which loses the toxicity thereof. Also, it is very important to build the three-dimensional network as best as possible and to wash the hydrogel after crosslinking so as to extract all of the residual potential monomers.

Chitosan is a material of natural and renewable origin. This biocompatible and biodegradable material, exhibits no toxicity, is soluble in acetic acid and is capable of being chemically grafted to other molecules.

The different types of molecules reacting with chitosan are numerous. Polyethylene glycol, polyvinyl alcohol, polyacrylic acid, hydroxyl cellulose, polyacrylates, polyacrylics, and polyacrylamide can in particular be mentioned.

Chitosan is a polysaccharide composed of the random distribution of β-(1-4) linked D-glucosamine (deacetylated unit) and N-acetyl-D-glucosamine (acetylated unit). It is produced by chemical (in alkaline medium) or enzymatic deacetylation of chitin, the component of the exoskeleton of arthropods (crustaceans) or of the endoskeleton of cephalopods (squid, etc.), sometimes also of plant origin (fungal walls) or of synthetic origin. This raw material is demineralized by treatment with hydrochloric acid, then deproteinized in the presence of sodium hydroxide or potassium hydroxide and finally discolored thanks to an oxidizing agent. The degree of acetylation (DA) is the percentage of acetylated units relative to the number of total units, it can be determined by Fourier transform infrared spectroscopy (FT-IR) or by titration by a strong base. Chitosan is soluble in acid medium unlike chitin which is insoluble. It is important to distinguish between the degree of acetylation (DA) and the degree of deacetylation (DD). One being the complementary of the other, that is to say that chitosan having a DD of 85%, has 15% of acetyl groups and 85% of amine groups on the chains thereof. Chitosan is a macromolecule whose molar mass is comprised between 50 kDa and 400 kDa (g/mole) which can also be visualized by a number of units from a few hundred to 2 or 3 thousand. The hydrogel comprises, for example, between 0.15% and 3% by weight of chitosan of the total weight of the hydrogel. In a more particular example, the hydrogel comprises between 0.30% and 2% by weight of chitosan of the total weight of the hydrogel.

N,N'-methylenebisacrylamide is a crosslinking agent. In the present invention, N,N'-methylenebisacrylamide allows obtaining a three-dimensional structure, in particular by the formation of covalent bonds between the chitosan-polyacrylamide chains.

A constituent copolymer of the hydrogel according to the invention is formed from a succession of repeating units, called monomers, linked to each other by covalent bonds. Within the meaning of the present invention, the term "copolymer" means a polymer resulting from the copolymerization of at least two types of chemically different monomers. Within the meaning of the invention, the copolymer is a homogeneous material with random, alternating and statistical sequence of the different monomers constituting it.

In one embodiment, the hydrogel of the invention comprises between 0.3% and 30% by weight, of the total weight of the hydrogel, of copolymer dry matter. In another embodiment, it comprises between 0.3 and 30.4%, in particular between 0.3033 and 30.4%, more particularly between 0.3415 and 30.4% by weight, of the total weight of the hydrogel, of copolymer dry matter. In another embodiment, the hydrogel of the invention comprises between 0.3033 and 30%, in particular between 0.3415 and 30% by weight, of the total weight of the hydrogel, of Below 0.30% by weight of the total weight of the copolymer dry matter hydrogel, the hydrogel may be more difficult to form or not form at all, that is to say that the mixture remains liquid. Above 30%, in particular above 30.4%, by weight of the total weight of the copolymer dry matter hydrogel, the hydrogel gradually risks becoming too hard and no longer being applicable or implantable or injectable. Advantageously, the proportion by weight of dry matter of the copolymer is equal to or greater than 2% by weight of the total weight of the hydrogel, or even 4%. Advantageously, this proportion by weight of dry matter of the copolymer is less than or equal to 15%, or even 10%.

In one embodiment, the hydrogel of the invention is substantially pyrogen-free. Within the meaning of the invention, the terms "substantially pyrogen-free" means a substantial exemption from substances inducing a rise in temperature. Different methods exist to identify the presence of pyrogens and are well known to the skilled person. In particular, a method allowing identifying the presence of pyrogen consists in injecting a rabbit with 10 mL of solution per kg of body weight and measuring the temperature thereof. If the rabbit's body temperature increases by 0.6° C., or if the total increase is more than 1.4° C. on three rabbits, the solution is not substantially pyrogen-free. Another method allowing identifying the presence of pyrogen consists in using a MAT assay ("Monocyte Activation Test") marketed, for example, by Merck™ under the names PyroDetect™ and/or PyroMAT™ introduced in the European Pharmacopoeia in 2010. This assay has been developed as an alternative to the methods using animals and aims at offering the possibility of carrying out the pyrogen assays in humans in an in vitro system. Within the meaning of the invention, a substantially pyrogen-free water is called non-pyrogenic water.

In one embodiment, the hydrogel according to the invention also comprises a diffusing agent and/or another agent or ingredient.

Within the meaning of the present invention, the term "diffusing agent" means an ingredient or an active ingredient capable of diffusing outside the hydrogel. The diffusing agent can be selected from inert ingredients having interesting biomechanical properties or active ingredients. These agents can be substances of plant origin such as the genepi extracts, substances of marine origin such as the extracts of New Zealand green mussels (Perna canaliculus), orthosilicic acid, organic silicon, silanol, vitamins such as vitamins A, D3, E or C, metals such as gold or silver, analgesics such as lidocaine, xylazine, detomidine, non-steroidal anti-inflammatory drugs, such as flunixin, ketoprofen, aspirin, corticosteroids such as prednisolone, triamcinolone, hyaluronic acid, glycosaminoglycans, chondroitin sulphate, methylsulphonylmethane, bromelain, arnica, collagen, antioxidants, fatty acids.

In one embodiment, the diffusing agent of the invention can also be comprised in a cargo. This cargo is defined as a matrix capable of onboarding the diffusing agent, in the hydrogel. According to the invention, different cargo techniques can allow onboarding the diffusing agent, such as encapsulation or vectorization, the technology called dripping technology, the creation of emulsions or specific coatings, polymeric grafting. In particular, the cargo can be selected from microcapsules, microparticles or even polymeric vehicles. The size of the used particles is for example comprised between 200 nm and 20,000 nm, which makes them particles of a size greater than those of nanoparticles whose European standard describes a size of less than 100 nm for more than 50% of them.

The diffusing agent, included or not in a cargo, is retained in the hydrogel, either by physical retention or by molecular interactions, covalent or not, examples of non-covalent interactions being ionic interactions, hydrogen bonds, or by any combination of these retention modes. In particular, the size of the pores, defined by the three-dimensional matrix structure of the copolymer of the hydrogel, can prevent the diffusing agent from being released until the hydrogel undergoes a degradation by one or more mechanism(s). The diffusing agent can thus be released either by a change in pH or temperature, or by mechanical action.

In one embodiment, the final hydrogel of the invention comprises between 0.0001% and 30% by mass of diffusing agent, on the total mass. Preferably, the diffusing agent comprises about 1% and 25% by mass, relative to the total mass of the final hydrogel. In a particular embodiment, the diffusing agent of the invention is an orthosilicic acid, an organic silicon or silanol.

In a particular embodiment, the diffusing agent is in the form of microparticles whose size (average diameter) is comprised between 200 nm and 20,000 nm. These microparticles are therefore larger in size than those of nanoparticles whose European standard describes a size of less than 100 nm for more than 50% of them.

In one embodiment, the mass ratio of acrylamide to chitosan is comprised between 1/1 and 1/8. Preferably, it is comprised between 1/2 and 1/6. In another embodiment, the mass ratio of chitosan to acrylamide is comprised between 1/100 and 1/2. It is, in particular, comprised between 1/8 and 1/2, in particular between 1/6 and 1/2.

In one embodiment, the mass ratio of N,N'-methylenebisacrylamide to acrylamide is comprised between 1/50 and 1/1000. Preferably, the mass ratio of N,N'-methylenebisacrylamide to acrylamide is comprised between 1/100 and 1/500.

In a particular embodiment, the hydrogel of the invention comprises the copolymer formed at least from acrylamide, chitosan and N,N'-methylenebisacrylamide and the diffusing agent, according to the following ratio in % by weight of the total weight of the final hydrogel:
Acrylamide 0.3% and 20%
Chitosan 0.0375% and 10%
N,N'-methylenebisacrylamide 0.004% and 0.4%
diffusing agent 0.001% and 30%
$H_2O$ in a complementary manner to 100%.

In another particular embodiment, the hydrogel of the invention comprises the copolymer formed at least from acrylamide, chitosan and N,N'-methylenebisacrylamide, and the diffusing agent, according to the following ratio in % by weight of the total weight of the final hydrogel:
Acrylamide 0.3% and 20%
Chitosan 0.003% and 10%
N,N'-methylenebisacrylamide 0.0003% and 0.4%
diffusing agent 0.001% and 30%
$H_2O$ in a complementary manner to 100.

According to a second object, the invention relates to a method for manufacturing a hydrogel as defined above.

In a first embodiment, the method comprises the following steps: copolymerization of acrylamide and chitosan, in the presence of N,N'-methylenebisacrylamide and a radical initiator, in an aqueous medium, to obtain a copolymer; washing the copolymer with water to obtain a washed copolymer; and adding the diffusing agent to obtain the hydrogel.

In a preferred embodiment, the method comprises the following steps: copolymerization of acrylamide and chitosan, in the presence of N,N'-methylenebisacrylamide, a diffusing agent, and a radical initiator, in an aqueous medium, to obtain a copolymer incorporating the diffusing agent then washing the copolymer incorporating the diffusing agent with water to obtain the hydrogel.

During the manufacturing method, the chitosan copolymerizes with the polyacrylamide by binding thereto covalently. Under the action of N,N'-methylenebisacrylamide (MBA), the system crosslinks in a three-dimensional network. MBA allows different chitosan-polyacrylamide chains to be covalently bound to form a three-dimensional network.

The chitosan is added in an acidic aqueous solution, that is to say an aqueous solution whose pH is less than 6. Preferably, the acidic aqueous solution comprises an organic acid, in particular an organic acid whose pKa is comprised between 4 and 6, such as a carboxylic acid. In particular, the acidic aqueous solution comprises acetic acid or hydrochloric acid.

The concentration of chitosan in the acidic aqueous solution is 0.1 to 5% by weight of the total weight of the solution.

The acidic aqueous solution of chitosan is mixed with acrylamide at a temperature comprised between 20 and 60° C. Preferably the temperature is comprised between 40 and 60° C.

The mass ratio of acrylamide to chitosan is comprised between 1/1 and 1/8. In another embodiment, the mass ratio of chitosan to acrylamide is comprised between 1/100 and 1/2, in particular between 1/8 and 1/2, particularly between 1/6 and 1/2.

The mass ratio of N,N'-methylenebisacrylamide to acrylamide is comprised between 1/50 and 1/1000. Preferably, the mass ratio of N,N'-methylenebisacrylamide to acrylamide is comprised between 1/100 and 1/500.

The copolymerization reaction is initiated by a radical initiator. In particular, the radical initiator is selected from potassium persulphate or ammonium persulphate. The mass ratio of the radical initiator to acrylamide is comprised between 1/100 and 1/10. The radical initiator can possibly be used in association with tetramethylethylenediamine (TEMED). TEMED is optional during the copolymerization. Thus, the mass ratio of TEMED to acrylamide is comprised between 1/2000 and 1/20. The absence of TEMED, a toxic catalyst, allows the formation of a hydrogel based on partly natural and biocompatible materials, and thus allows a more responsible bio-design.

Washing the Hydrogel

The hydrogel is formed from a copolymerization of chitosan with acrylamide. The copolymer is crosslinked thanks to N,N' bis-acrylamide. The optimization of this crosslinking consists in making it as complete as possible so that, on the one hand, the three-dimensional network is best formed and that, on the other hand, the toxic monomers (acrylamide and N,N' bis-acrylamide) are present as little as possible. However, caution requires "washing" the hydrogels formed so that the possible residual monomers within the hydrogel can be discharged. The "washing" of the hydrogel therefore consists in immersing this hydrogel in water and using the osmosis phenomenon to discharge these monomers. According to the principle of osmosis, the molecules are displaced from the areas where concentrations are high to the areas with lower concentrations. This displacement is described by Fick's law which expresses a linear relationship between the material flow and the concentration gradient thereof.

As shown in FIG. 6A, at least two phenomena occur. The residual monomers trapped within the hydrogel (symbolized by the light gray color) will be discharged into the "washing" water (symbolized by the dark gray color). Conversely, the water outside the gel will enter into the hydrogel.

This osmosis washing phenomenon results in a swelling of the hydrogel. Some preliminary tests of "washed" hydrogels show the variation in mass (in percent) as a function of time. As shown in FIG. 9, this variation in the relative deviation of mass gain increases linearly as a function of time until it obtains nearly 200% (3-time swelling) in the case of the hydrogel N4a and in the range of 300% (3-time swelling), in the case of the hydrogel N4a/2 for an immersion time of approximately 4 days.

It is clear that the significant expansion of hydrogels will result in an inversely proportional reduction in the amount of dry matter intrinsic to the gel.

Washing the copolymer with water allows removing contaminants and ensuring an absence of such contaminants within the hydrogel. The contaminants of the copolymer can be residual monomers, radical initiator residues, organic acids. In particular, repeated washing with water and analysis of the washing water, in particular by FT-IR, allows measuring the rate of residual monomers not having participated in the copolymerization and/or crosslinking reaction and also allows ensuring the absence of these residual monomers in the hydrogel. In particular, the hydrogel of the invention comprises less than 20 mg/mL of acrylamide and less than 20 EU/device of endotoxins.

The diffusing agent, possibly comprised in a cargo, can be added in the solid state or suspended in water. In particular, the diffusing agent can be added in suspension in non-pyrogenic water.

In a particular embodiment, the method of the invention comprises the following steps: copolymerization of acrylamide and chitosan, introduced with a mass ratio comprised between 1/1 and 1/8, at a temperature comprised between 20 and 60° C., preferably between 40 and 60° C., in the presence of N,N'-methylenebisacrylamide, introduced with a mass ratio relative to the acrylamide comprised between 1/50 and 1/1000, preferably comprised between 1/100 and 1/500, and of a radical initiator selected from potassium persulphate or ammonium persulphate, possibly in association with tetramethylethylenediamine, in an aqueous medium to obtain a copolymer; washing the copolymer with water over 3 to 15 washes for 48-240 hours to obtain a washed copolymer; and adding the diffusing agent between 0.001% and 30%, to obtain the final hydrogel.

In a second embodiment, the method comprises the following steps: copolymerization of acrylamide and chitosan, in the presence of N,N'-methylenebisacrylamide, a diffusing agent, and a radical initiator, in an aqueous medium, to obtain a copolymer incorporating the diffusing agent; washing the copolymer incorporating the diffusing agent with water to obtain the hydrogel.

Advantageously, before the copolymerization reaction, the chitosan is dissolved in an aqueous solution at a pH comprised between 2 and 5, under magnetic or mechanical stirring, then neutralized and filtered under vacuum. The aqueous solution having a pH comprised between 2 and 5 is ideally an aqueous solution of hydrochloric acid or acetic acid.

Advantageously, the copolymer incorporating the diffusing agent is extruded through specific pore grids before the washing step.

According to an advantageous embodiment, the washing step is carried out by dialysis, by means of dialysis membranes. In this case, a gel containment system is set up so as to limit the swelling of said gel by affecting as little as possible the displacement of the residual monomers towards the washing water. This is shown schematized in FIG. 6B. In order to improve the washing efficiency, the water is changed regularly (once every 12 hours, for example) and the stirring is facilitated using magnetic stirring, mechanical stirring (blades), water pump stirring, etc. A first washing test has been conducted to compare the efficiency of a dialysis tube compared to a tube which is large enough not to limit the swelling. FIGS. 7A, 7B and 7C illustrate the placement of the membrane on the neck, the filling of the membrane using a gun and the closure of the membranes with clips and knots. FIG. 8 shows the results obtained in terms of the relative deviation of mass gain as a function of time.

It should be noted that, in standard cases, the washing of the hydrogel lasts several days (5 to 6 days) so that the greatest portion of residual monomers can be discharged. The rate of residual monomers decreases more rapidly as the osmosis conditions are favorable, that is to say that the water is changed regularly and the stirring is sufficient. The experimental results allow defining the minimum washing time of 2 days.

The washing step implemented during the preparation of the hydrogel is carried out by implementing the weighing of the hydrogels each time the water in the tank is changed. These mass measurements allow construct the curve of evolution of the relative deviation of mass gain as a function of time (FIGS. 11A and 11B). The curve shows a plateau corresponding to the confinement of the hydrogel within the membrane. We note that this plateau takes values which are comprised between 50 and 70% much lower than the previous ones of the 200 to 300%, illustrating good control of the expansion of the gel during washing.

According to a third object, the invention relates to the use of a hydrogel in a mechanical visco-supplementation system, for external or internal use.

The mechanical visco-supplementation system according to the invention allows physically onboarding the diffusing agent in situ, to support the normal physiological and rheological conditions of wounds, joints or in the case of gastric ulcers, in particular in horses.

In one embodiment, the hydrogel of the invention is used internally in an implantable mechanical visco-supplementation system for supporting the soft tissues of mammals, and/or bones and cartilage according to the diffusing agent. Soft tissues are elements of the body, such as fatty tissue, connective tissue, synovial membrane, joint capsule muscles, tendons, dermis or epidermis.

The mechanical visco-supplementation for internal use consists in locally implanting the hydrogel which acts as a support agent for the synovial membrane, synovial fluid or bone and cartilage as appropriate. The hydrogel thus allows the joint to support its mobility through a biomechanical action.

Advantageously, the mechanical visco-supplementation system for internal use is a lubricant.

In another embodiment, the hydrogel of the invention is used externally in a mechanical visco-supplementation system. For external use, mechanical visco-supplementation consists in applying the hydrogel locally, which acts as a healing support agent. This healing support results in maintaining a wound moisture during healing thanks to the large amount of water present in the hydrogel. Advantageously, the mechanical visco-supplementation system for external use is a moisturizer.

The use of the hydrogel according to the invention allows a delayed effect of the diffusing agent comprised in the hydrogel. In particular, the diffusing agent begins to diffuse between the 2nd and the 30th day after administration, preferably between the 10th and the 20th day, in particular from the 15th day.

The use of the hydrogel according to the invention also allows a prolonged effect of the diffusing agent comprised in the hydrogel. Preferably, the diffusing agent is released over a period comprised between 2 weeks and 12 months, preferably between 1 month and 6 months.

Thus, the mechanical visco-supplementation systems of the invention require fewer applications and the effect is manifested for a prolonged period, of at least two weeks.

This prolonged mechanical visco-supplementation of the diffusing agent, which is located, fastened, protected then released by the hydrogel is made possible thanks to the viscoelastic matrix structure of the hydrogel. The effects of the viscoelastic hydrogel, including the delayed and prolonged release of the diffusing agent, persist significantly. Under these conditions, the hydrogel diffuses little by little within a few weeks after use and this is the case for several weeks, as if it resulted in continuous use in the wounds or the joint, for such a period of time. This results, for example, in a substantial simplification of the joint support by providing a sustainable visco-supplementation and significantly reducing the number of applications or implantations.

According to a fourth object, the invention relates to an external or internal visco-supplementation kit comprising an acrylamide and chitosan copolymer crosslinked with N,N'-methylenebisacrylamide, and a diffusing agent in solid phase or in suspension, said copolymer and said diffusing agent being previously mixed in the form of a hydrogel or mixed extemporaneously to form a hydrogel.

This kit comprises a copolymer formed at least from acrylamide, chitosan and crosslinked with N,N'-methylenebisacrylamide, and a diffusing agent in solid phase or in suspension. The copolymer and the diffusing agent are either previously mixed in the form of a hydrogel, or mixed extemporaneously to form a hydrogel.

EXAMPLES

Example 1: Preparation of the Constituent Copolymer of the Hydrogel According to the Invention a) Products Involved in the Mixture
   40% acrylamide solution in water, Sigma Aldrich™ (Molecular biology/embryo transfer/pharma grade)
   2% N,N'-methylenebisacrylamide solution in water, Sigma Aldrich™ (Molecular biology/embryo transfer/pharma grade)
   1% Chitosan solution in 0.1 M acetic acid, Sigma Aldrich™ (350 kDa>75% deacetylation, Molecular biology/embryo transfer/pharma grade)
   Potassium persulphate (KPS) (>99%) in powder, Sigma Aldrich™ (Molecular biology/embryo transfer/pharma grade)
   Water for injections (WFI water)
b) Equipment
   1 L glass flask
   Magnetic stirrer (of Fischer Bioblock Scientic™ brand), rotation 500 rpm
   Temperature of 40° C. (regulation by Heidolph™ EKT 3001 thermocouple)
c) General Protocol
1. Step 1
   Pouring the Chitosan solution into the flask preheated to 40° C., keeping this temperature and maintaining stirring at 500 rpm
2. Step 2
   Mixing the acrylamide solution with the N,N'-methylenebisacrylamide solution. Pouring the mixture into the flask 1 minute after the chitosan
3. Step 3
   Dissolve the APS (ammonium persulphate) or KPS in a portion of the additional water, by stirring until complete dissolution.
   Gradually pouring this solution, 1 minute after pouring in the solution (acrylamide and N,N'-methylenebisacrylamide)
4. Step 4
   Pouring the WFI water to the desired total volume
5. Step 5
   Keeping the magnetic stirring and the temperature for a duration of 45 minutes for a copolymerization of Chitosan on the polyacrylamide and for a crosslinking with N,N'-methylenebisacrylamide
6. Step 6
   Leaving for 24 hours to let the gel completely form
7. Step 7
   Performing several (3 to 5) rinses in WFI water for 96 hours then draining the gel and storing it at ambient temperature.
d) Different Tested Formulations

| Constituents (in g) | V1 | V2 | V3 |
|---|---|---|---|
| 40% Acrylamide | 41.43 | 50.75 | 50.75 |
| 2% N,N'-methylenebisacrylamide | 3.31 | 4.06 | 6.12 |
| 1% Chitosan in 0.1M acetic acid | 49.71 | 406.00 | 406.00 |
| TEMED | 0.00 | 3.13 | 0.00 |
| KPS | 3.13 | 0.00 | 1.50 |
| APS | 0.31 | 0.00 | 0.00 |
| WFI water difference | 482.90 | 116.06 | 1115.63 |
| Total mixture (in g) | 580 | 580 | 580 |

Example 2. Characterisation of the Constituent Copolymer of the Hydrogel According to the Invention a) Fourier Transform Infrared (FTIR) Characterization of the Copolymer Present in the Hydrogel FTIR measurements, on dry matter, were carried out to compare the spectra of the chitosan-polyacrylamide-MBA copolymer present in the copolymer hydrogel of the invention at 3.75%, without diffusing agent (V14), at 3.75%, with diffusing agent (V20) versus "pure" polyacrylamide at more than 3.5% without chitosan (V5) and "pure" chitosan (Chitosan). The dry matter weighing is contained in FIG. 2A.

The spectra are represented in FIGS. 2B and 2C. A more accurate analysis of the spectra has focused on the differences between the hydrogel without diffusing agent (V14) versus pure polyacrylamide hydrogel (V5) and chitosan. The specific bonds are shown in FIG. 2D.

The experimental conclusions confirm the published literature on the grafting of the copolymer type.
1. The peaks of V14 at 1450 cm$^{-1}$ and 3182 cm$^{-1}$ are the unique characteristics of a copolymerization between chitosan and polyacrylamide.
2. The peak at 3350 cm$^{-1}$ (N—H) observed on the chitosan and less on the copolymer is characteristic of the consumption of this bond for the grafting according to the bibliography.
3. The peaks at 1375 cm$^{-1}$ (C—H) and 1113 cm$^{-1}$ (C—O) observed on chitosan but which disappear on the copolymer and the pure polyacrylamide gel: the literature attributes this to the grafting of chitosan with polyacrylamide.

Six specific and distinctive peaks of the chitosan-polyacrylamide-MBA copolymer are identified in the FTIR measurements, which confirms the copolymerization.

This FTIR analysis verifies that the chitosan and the polyacrylamide were covalently bonded giving rise to a single copolymer.

b) Dissolution Assay of the Copolymer in 1% Acetic Acid
   Dissolution test of chitosan in acetic acid diluted to 1/100:
   49.5 water, 0.5 g of pure acetic acid, 0.5 g of chitosan are weighed.
   Mixing in a beaker and allowing to act, as represented in FIG. 3A.
   After 30 minutes, under mechanical stirring by hand, the chitosan is dissolved.
   Dissolution test of the chitosan-polyacrylamide-MBA copolymer in acetic acid diluted to 1/100:
   49.5 water, 0.5 g of pure acetic acid, 20 g of chitosan-polyacrylamide-MBA are weighed.
   Mixing in a cup and allowing to act, as represented in FIG. 3A.
   After 60 min, under mechanical stirring by hand, a filter is used, as illustrated in FIG. 3B.
   A gel is collected that is weighed and the weight of 20.00 g is found.
   It is possible to conclude that the copolymer is well crosslinked since it is insoluble in acetic acid.

c) Characterization of the Dynamic Viscoelasticity of the Copolymer

The dynamic viscoelasticity of the copolymer obtained after washing is measured and compared with the dynamic viscoelasticity of the copolymer obtained before washings, with that of the copolymer obtained after adding acetic acid and with that of the copolymer obtained after shearing.

As reminded by the conclusions of the tests in FIG. 4 which illustrates the loss tangents (G"/G') of the chitosan-polyacrylamide-MBA copolymer before washing (top left), after washing (top right), after 1 h in acetic acid (bottom left) and after syringe shear (bottom right), this viscoelasticity measurement reveals significant values of the elastic modulus characteristic of the crosslinking. Thus, it proves the existence of a three-dimensional network in the case of the chitosan-graft-polyacrylamide copolymer hydrogel, as in the case of pure polyacrylamide hydrogel. In parallel with the obtained shear modulus values, the loss tangent values show a marked presence of elasticity relative to viscosity, characteristic of a crosslinked system.

In addition, this study also shows that the crosslinking of the copolymerized system is effective, because the gel formed is not dissolved in acetic acid, unlike the linear molecules of chitosan.

This crosslinking state remains during the various operations (washing, shearing through the entry and exit of the syringe).

Example 3: Improved Biocompatibility of the Hydrogel According to the Invention Relative to a Hydrogel Containing Only Polyacrylamide The hydrogel according to the invention has an improved biocompatibility relative to a hydrogel containing only polyacrylamide. Indeed, the hydrogel according to the invention comprises chitosan copolymerized with polyacrylamide, chitosan includes polyglucosamine sequences having a biocompatibility, which shows in vitro results of better biocompatibility, with in particular an absence of cytotoxicity.
Summary of the Experiment:

An XTT cytotoxicity assay is performed by Eurofins Medical Device", according to the standard ISO 10993-5: 2009, under conditions of good laboratory practice (GLP). The assay relates to the hydrogel described by the invention, namely a 5% polyacrylamide-chitosan copolymer hydrogel NVC-0 and a 4% polyacrylamide hydrogel containing silver ions (Bioform/Noltrex™ brand). An extraction was carried out under stirring for 24 h in a cell culture medium, the extracts being incubated for 24 h-48 h with L929 cells. The value of the decrease in the mitochondrial dehydrogenase rate in the culture media, compared to the control measurement of the reference, was used as a measurement of cytotoxicity, this at 4 different concentrations of hydrogel in the medium (100%, 66.7%, 44.4%, 29.6%). A mitochondrial dehydrogenase activity which is greater than 70% indicates a biocompatibility of the product according to the standard.
Results:

For a concentration of 100% (i.e. no dilution of the hydrogels in the medium), the mitochondrial dehydrogenase of the polyacrylamide-chitosan hydrogel NVC-0 is 101% (SD 0.07) and that of the 4% polyacrylamide hydrogel is 95% (SD 0.05).

As shown in FIGS. 13A and 13B, the hydrogel NVC-0 according to the invention has a total absence of cytotoxicity (no decrease in mitochondrial dehydrogenase, and this is the case at all dilutions), unlike the other hydrogel. The hydrogel of the invention has in this XTT assay an improved biocompatibility of +6% relative to the hydrogel containing only polyacrylamide.

Example 4: Improved Biodegradability of the Hydrogel According to the Invention Relative to a Hydrogel Comprising Only Polyacrylamide The hydrogel of the invention has the advantage of a biodegradability of chitosan that it contains, moreover in glucosamine and N-acetylglucosamine, substances which are naturally present in the human body. Glucosamine is known for its support in particular of the osteo-articular system. The biodegradability of chitosan being able to vary from a few tens of days to a few months depending on the enzymatic media and the characteristics of the polyglucosamine. The formula shown in FIG. 14 describes chitosan, therefore indicating the presence of glucosamine as a constituent unit of the polymer.
Summary of the Experiment:

A Fourier transform infrared spectroscopy (FT-IR) between 4000 and 400 $cm^{-1}$ is carried out in order to determine the chemical nature of the constituent bonds of the 5% copolymer hydrogel NVC—O and a hydrogel containing only polyacrylamide. A collection of each sample was placed in an oven at 30° C. for 40 hours in order to carry out analyses by FT-IR spectroscopy in ATR (Attenuated Total Reflection) mode on dry extract. The spectrum is recorded between 4000 $cm^{-1}$ and 400 $cm^{-1}$. ATR is a non-destructive technique which is adapted to materials having a high absorbency.
Results:

A characteristic peak appears around 1072 $cm^{-1}$ (marked on the spectra) which is present for the sample of the copolymer hydrogel NVC-0 as shown in FIG. 15. This is a characteristic absorption band which is observed only on this one. This band around 1072 $cm^{-1}$ may be characteristic of the deformation-type vibration modes of the C—O—C groups (of chitosan). The TF-IR analysis indicates the presence of the bonds of chitosan in the hydrogel proposed by the invention. This hydrogel provides a biodegradability, in particular in glucosamine which is naturally present in the human body, compared to a hydrogel only of polyacrylamide.

Example 5: Carrying Capacity of the Hydrogel According to the Invention

The copolymer hydrogel according to the invention has a carrying capacity, in particular of submicron capsules. The microstructure of the three-dimensional network of this hydrogel has alveoli whose size is compatible with the carried particles, which polyacrylamide gels made according to the prior art do not propose.
Summary of the Experiment:

The Joint Center for Applied Microscopy (CCAM) of the University of Nice carried out cryoimaging by Scanning Electron Microscope (SEM) of the hydrogel NVC-0 according to the invention, containing organic silicon microcapsules. Samples of the hydrogel NVC-0 and the hydrogel NVC-0-C containing microcapsules were successively immersed into liquid nitrogen, sublimated then fractionated to be passed to SEM. The analysis has been performed 7 weeks in post-production of the batches.
Results:

The Polyacrylamide-chitosan copolymer hydrogel offers a carrying capacity which is illustrated by SEM. The results of this imaging also show a biocompatible protection of the hydrogel against microcapsules, which did not deteriorate for 7 weeks within the hydrogel. As shown in FIG. 15A (SEM (×10,000) cryoimaging of the copolymer hydrogel NVC-0), a dense and relatively homogeneous crosslinked network is observed, with alveoli of a size of 0.1-0.5 microns on the copolymer hydrogel samples. As shown in FIG. 15B (SEM (×23,000) cryoimaging of the copolymer hydrogel NVC-0-C (7 weeks post production)), a microcapsule of a size of 0.6 microns is observed by SEM on the hydrogel containing microcapsules, 7 weeks after the production and integration of organic silicon microcapsules of 0.6-0.8 microns.

Example 6: Supplementation Capacity of the Hydrogel According to the Invention

The copolymer hydrogel according to the invention offers a supplementation capacity, either by the degradation of chitosan into glucosamine (Example 4), or by the water contained in the hydrogel (Example 8), or by the degradation of microcapsules, such as those containing for example orthosilicic acid. Organic silicon, during the degradation thereof, allows supplementing with silicon, a substance which is naturally present in the body but not renewed with age. It appears that the hydrogel according to the invention proposes a capacity for salting-out the on-board microcapsules, with a delayed salting-out over time. Thanks to the biodegradability of the hydrogel containing chitosan (Example 4), the onboard microcapsules (Example 5) could be released over time. This characteristic offers a long-term and local supplementation of substances onboard by the hydrogel according to the invention.
Summary of the Experiment:

A first preliminary study was carried out in order to evaluate the salting-out kinetics of microcapsules onboarding orthosilicic acid in a synovial fluid type synthetic medium. The particles were incubated in the artificial fluid containing 3 g/L of hyaluronic acid at a concentration of 0.6 mg/mL in particles. A dialysis/filtration system allowed separating the dissolved fractions from the particles (below). The dissolved orthosilicic acid was then dosed by ICP-AES.
Results:

The analysis allowed demonstrating that a significant amount of orthosilicic acid is detectable in the "dissolved" compartment. After 15 days of incubation, particles are still visible in the "particles" compartment and were titrated by ICP. These preliminary data suggest a slow degradation of the particles to supplement with orthosilicic acid

| | | T0 | T + 15 d |
|---|---|---|---|
| Concentration orthosilicic acid (mg/mL) | "Particles" compartment | 0.6 | 0.58536 |
| | "Dissolved" compartment | 0 | 0.01464 |

Example 7: Manufacture of the Hydrogel—Dialysis

The hydrogel according to the invention is manufactured by implementing a high-performance dialysis step, allowing removing the residual monomers from the synthesis, under very low quantification limits (less than 4 ppm), as mentioned in the table of FIG. 16
Summary of the Experiment:

The copolymer in the hydrogel form is extruded several times through extrusion grids between 50 and 500 microns depending on the hydrogels. This extrusion allows an optimal dialysis which begins with the choice of dialysis bags with pores adapted depending on the consistency of the hydrogel, ideally from 6 to 50 kD MWCO (Molecular weight cut-off in kilo Daltons). The extruded hydrogel is bagged then placed in water for different durations, ideally for 2 to 7 days, depending on the quality of the synthesis and the viscosity of the retained chitosan.

The GCMS or UPLC/UV method allows measuring the residual monomers such as acrylamide or methyl-bis-acrylamide.
Results:

The 5% polyacrylamide-chitosan copolymer hydrogel has been tested and the concentration measurements of possible residual monomers indicate values below the quantification limits of 4 ppm by the different methods.

Example 7: "Hydrophilic Swelling" of the Hydrogel According to the Invention

As illustrated in FIG. 10, the copolymer hydrogel PAAG-CH according to the invention has a capacity 3 times greater in the water carrying (hydrophilic swelling) compared to a hydrogel of the same concentration of polyacrylamide only. So less substance is needed with a hydrogel copolymer to provide as much hydration as with a polyacrylamide gel with equal initial concentration.
Summary of the Experiment:

Two hydrogels are synthesized, one 5% polyacrylamide copolymer containing chitosan (NVC-0) and the other containing only polyacrylamide (PAAG). Following their extrusion, then dialysis, weighing is performed every 12 hours to measure the relative deviation of the weight gain in water. Studies have also been conducted by varying the rates of crosslinking or percentage of polyacrylamide. The presence of the copolymerized chitosan in the hydrogel provides a significant increase in the relative deviation in water intake.
Results:

From 3 days of dialysis, the 5% polyacrylamide hydrogel reaches a swelling plateau of 25% maximum of the weight thereof. The 5% polyacrylamide-chitosan copolymer exceeds the water carrying capacity of a polyacrylamide hydrogel from dialysis and continues to swell beyond 75% of the weight thereof in water after 5 days for example.

Example 8: Copolymerization of Chitosan on Polyacrylamide in a Hydrogel According to the Invention As shown in FIG. 17, according to the invention, the copolymerization of chitosan on polyacrylamide occurs by the creation of covalent bonds between the macromolecular chain of chitosan via free radicals formed by the action of a peroxide and the polyacrylamide chain being formed from acrylamide monomers.

The copolymer is formed, creating a macromolecular chain which is then organized in the form of a three-dimensional network thanks to the crosslinking agent (methyl-bis-acrylamide).

polyacrylamide: between 0.3% and 20%
chitosan: between 0.0375% and 10%
N,N'-methylenebisacrylamide: between 0.004% and 0.4%
diffusing agent: between 0.001% and 30%
H2O: complement to 100%.

2. The hydrogel according to claim 1, wherein the copolymer formed at least from acrylamide, chitosan and N,N'-methylenebisacrylamide has the formula:

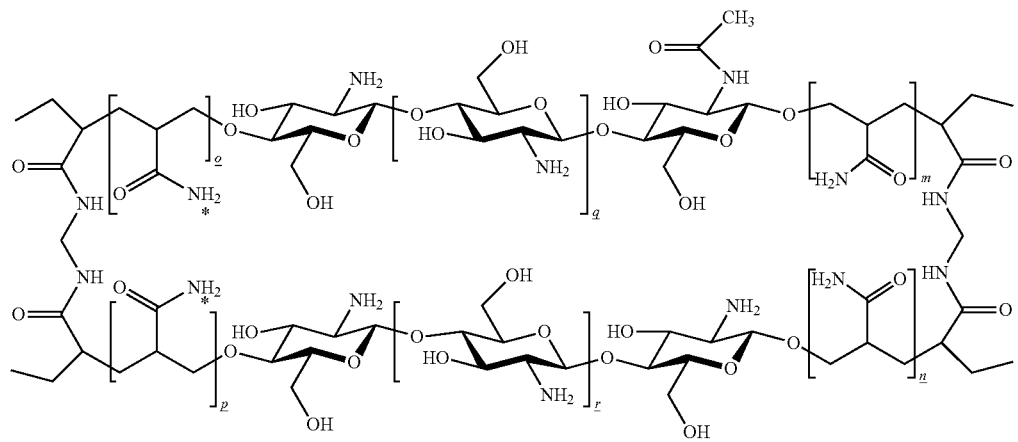

Thus the polyacrylamide/chitosan copolymer is a specific polymer different from polyacrylamide. The hydrogel obtained by crosslinking these copolymer and crosslinking agent chains forms a different network of acrylamide which is verified in particular by the much higher swelling rate in the case of the copolymer than in the case of acrylamide (Example 7).

Summary of the Experiment:

A polyacrylamide-chitosan copolymer hydrogel and a polyacrylamide hydrogel are tested by the NMR method. The samples are evaporated, the dry matters hydrated with water D20 then evaporated again. The dry matters were solubilized in a D20/AcOD 1/1 preparation. The 1H NMR spectrum has been recorded on a Bruker™ 400 MHz apparatus at 50° C.

Results:

The NMR of the copolymer (FIG. 18A) has several distinctive points, in particular specific for chitosan at 3.2, 3.6 and 4.9 ppm (FIG. 18B) and in a significant proportion relative to the NMR of the hydrogel of polyacrylamide alone (FIG. 18C). The NMR of the copolymer hydrogel which is described in the patent confirms the different nature of the polymer relative to hydrogel of polyacrylamide or simple mixture with polyacrylamide.

The invention claimed is:

1. A biocompatible hydrogel comprising:
   from 0.3% to 30% by weight of dry matter of a copolymer formed at least from acrylamide, chitosan and N,N'-methylenebisacrylamide, and
   a diffusing agent,
wherein the hydrogel comprises the following ratios of constituents in % by weight of a total weight of the hydrogel:

where
m, n, o, p, g, r are positive integers.

3. The hydrogel according to claim 1, wherein the diffusing agent is selected from the group consisting of inert ingredients which have biomechanical properties and active ingredients.

4. The hydrogel according to claim 1, wherein the diffusing agent is comprised in a cargo selected from microcapsules, microparticles and polymeric vehicles.

5. The hydrogel according to claim 1, wherein the diffusing agent forms microparticles of a size comprised in a range of from 200 nm to 20,000 nm.

6. The hydrogel according to claim 1, which is substantially free of pyrogen.

7. The hydrogel according to claim 1, wherein, in the copolymer, a mass ratio of the N,N'-methylenebisacrylamide to the acrylamide is comprised in a range of from 1/50 to 1/1000.

8. The hydrogel according to claim 2, wherein the diffusing agent is selected from the group consisting of substances of plant origin, substances of marine origin, orthosilicic acid, organic silicon, silanol, vitamins, metals, analgesics, xylazine, detomidine, non-steroidal anti-inflammatory drugs, ketoprofen, aspirin, corticosteroids, triamcinolone, hyaluronic acid, glycosaminoglycans, chondroitin sulphate, methylsulphonylmethane, bromelain, arnica, collagen, antioxidants, fatty acids.

9. A biocompatible hydrogel comprising:
   from 0.3% to 30% by weight of dry matter of a copolymer formed at least from acrylamide, chitosan and N,N'-methylenebisacrylamide, and
   a diffusing agent,
   wherein the diffusing agent forms microparticles of a size comprised in a range of from 200 nm to 20,000 nm.

10. A method of manufacturing a hydrogel, comprising:
   copolymerizing acrylamide and chitosan, in the presence of N,N'-methylenebisacrylamide and a radical initiator, in an aqueous medium, to obtain a copolymer;

washing the copolymer with water to obtain a washed copolymer; and adding a diffusing agent, so as to obtain the hydrogel according to claim 1.

11. The method according to claim 10, comprising adding the diffusing agent prior to the copolymerizing of the acrylamide and the chitosan in the presence of the N,N'-methylenebisacrylamide and of the radical initiator, so that the three-dimensional network formed by the copolymer is built around the diffusing agent.

12. The method according to claim 10, comprising:

copolymerizing the acrylamide and the chitosan at a temperature comprised in a range of from 20° C. to 60° C., in the presence of the N,N'-methylenebisacrylamide, which is introduced with a mass ratio relative to the acrylamide comprised in a range of from 1/50 to 1/1000, and of the radical initiator with a mass ratio relative to the acrylamide comprised in a range of from 1/100 to 1/10, wherein the radical initiator is at least one selected from the group consisting of potassium persulphate and ammonium persulphate, in an aqueous medium to obtain a copolymer;

washing the copolymer with water to obtain a washed copolymer; and adding the diffusing agent in an amount comprised in a range of from 0.001% to 30% by weight of a total weight of the hydrogel, wherein the diffusing agent is at least one selected from the group consisting of inert ingredients which have biomechanical properties and active ingredients, to obtain the hydrogel.

13. The method according to claim 10, wherein the washing of the copolymer is carried out by dialysis, using dialysis membranes.

14. A mechanical visco-supplementation system, which is adapted for external or internal use, wherein the mechanical visco-supplementation system comprises the hydrogel according to claim 1.

15. The mechanical visco-supplementation system according to claim 14, which is configured for internal use.

16. The mechanical visco-supplementation system according to claim 15, which is adapted for supporting at least one selected from the group consisting of soft tissues, bones, and cartilage of mammals.

17. The mechanical visco-supplementation system according to claim 14, which is a moisturizer.

18. The mechanical visco-supplementation system according to claim 14, which is configured so that the diffusing agent begins to diffuse at a time in a range of from the 2nd to the 30th day after administration.

19. The mechanical visco-supplementation system according to claim 14, which is configured so that the diffusing agent is released over a period comprised in a range of from 2 weeks to 12 months.

20. An external or internal mechanical visco-supplementation kit comprising:

the biocompatible hydrogel according to claim 1, wherein the diffusing agent is in solid phase or in suspension, and wherein the copolymer and the diffusing agent form a mixture in the hydrogel.

\* \* \* \* \*